(12) United States Patent
Jeong et al.

(10) Patent No.: US 11,565,007 B2
(45) Date of Patent: Jan. 31, 2023

(54) STERILIZATION MODULE

(71) Applicant: SEOUL VIOSYS CO., LTD., Ansan-si (KR)

(72) Inventors: Woong Ki Jeong, Ansan-si (KR); Jae Hak Jeong, Ansan-si (KR); Si Ho Yu, Ansan-si (KR); Byung Chul Joo, Ansan-si (KR); Jae Young Choi, Ansan-si (KR); Kyu Won Han, Ansan-si (KR); Yeo Jin Yoon, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 530 days.

(21) Appl. No.: 16/628,529

(22) PCT Filed: Jul. 6, 2018

(86) PCT No.: PCT/KR2018/007672
§ 371 (c)(1),
(2) Date: Jan. 3, 2020

(87) PCT Pub. No.: WO2019/009651
PCT Pub. Date: Jan. 10, 2019

(65) Prior Publication Data
US 2021/0393817 A1 Dec. 23, 2021

(30) Foreign Application Priority Data

Jul. 7, 2017 (KR) .......................... 10-2017-0086724
Nov. 10, 2017 (KR) .......................... 10-2017-0149568

(51) Int. Cl.
*A61L 2/10* (2006.01)
*A61L 2/26* (2006.01)
(Continued)

(52) U.S. Cl.
CPC ................... *A61L 2/10* (2013.01); *A61L 2/26* (2013.01); *H01L 33/483* (2013.01); *H01L 33/56* (2013.01); *A61L 2202/122* (2013.01)

(58) Field of Classification Search
CPC ........ A61L 2/10; A61L 2/26; A61L 2202/122; H01L 33/56; H01L 33/483
See application file for complete search history.

(56) References Cited

U.S. PATENT DOCUMENTS 7,826,756 B2 11/2010 Bae
2018/0215634 A1 8/2018 Jung et al.

FOREIGN PATENT DOCUMENTS

CN 202855800 4/2013
CN 204834683 12/2015
(Continued)

OTHER PUBLICATIONS

Chinese Office Action dated Jul. 15, 2021, issued in Chinese Patent Application No. 201880035611.6 (with English Concise Explanation).
(Continued)

*Primary Examiner* — Sean E Conley
(74) *Attorney, Agent, or Firm* — H.C. Park & Associates, PLC

(57) ABSTRACT

A sterilization module including a main body including an ultraviolet outlet, a transparent member disposed on the ultraviolet outlet to transmit ultraviolet light, and a light source unit irradiating ultraviolet light toward the transparent member, and a sealing member, in which the light source unit includes a circuit board and a light emitting diode chip mounted thereon and including an epitaxial substrate, a conductive semiconductor layer electrically connected to the circuit board directly by an electrode, ultraviolet light is c irradiated toward the transparent member by passing through the epitaxial substrate, the sealing member is dis-
(Continued)

posed between the transparent member and the circuit board, and a distance between the transparent member and the circuit board spaced apart from each other by the sealing member is greater than a height of the light emitting diode chip.

21 Claims, 29 Drawing Sheets

(51) Int. Cl.
*H01L 33/48* (2010.01)
*H01L 33/56* (2010.01)

(56) References Cited

FOREIGN PATENT DOCUMENTS

| | | |
|---|---|---|
| CN | 205061615 | 3/2016 |
| CN | 205645858 | 10/2016 |
| CN | 205856047 | 1/2017 |
| CN | 205892799 | 1/2017 |
| JP | 5968795 | 8/2016 |
| KR | 10-2007-0088999 | 8/2007 |
| KR | 10-2008-0001096 | 1/2008 |
| KR | 10-2009-0075293 | 7/2009 |
| KR | 10-1691597 | 1/2017 |
| KR | 10-2017-0037777 | 4/2017 |
| KR | 10-2017-0116506 | 10/2017 |

OTHER PUBLICATIONS

Korean Office Action dated Jun. 28, 2022, issued to Korean Patent Application No. 10-2017-0149568.
International Search Report dated Nov. 8, 2018, in International Application No. PCT/KR2018/007672 (with English Translation).
Saudi Arabian Office Action dated Nov. 8, 2022, in Saudi Arabian Patent Application No. 520410967.

STERILIZATION MODULE

CROSS-REFERENCE TO RELATED APPLICATIONS

This application is a National Stage Entry of International Application No. PCT/KR2018/007672, filed on Jul. 6, 2018, and claims priority from and the benefit of Korean Patent Application No. 10-2017-0086724, filed on Jul. 7, 2017, and Korean Patent Application No. 10-2017-0149568, filed on Nov. 10, 2017, each of which is hereby incorporated by reference for all purposes as if fully set forth herein.

BACKGROUND

Field

Exemplary embodiments of the invention relate generally to a sterilization module.

Discussion of the Background

Ultraviolet (UV) light has different features depending on a wavelength, and may be applied to a sterilization module using its varying features according to a wavelength. In general, a mercury (Hg) lamp is used in the sterilization module using the UV. Sterilization may take place using ozone ($O_3$) generated by the wavelength from the mercury lamp. However, because the mercury (Hg) lamp includes mercury inside, the environment may be polluted as the usage time increases.

The sterilization module using various UV rays has been recently developed. Furthermore, objects for sterilization have also been varied. As such, the sterilization module is recently embedded in a specific device, such as a refrigerator, washing machine, a humidifier, a water purifying device, or the like.

The above information disclosed in this Background section is only for understanding of the background of the inventive concepts, and, therefore, it may contain information that does not constitute prior art.

SUMMARY

Sterilization modules constructed according to exemplary embodiments of the invention are capable of being miniaturized and increasing sterilization efficiency.

Exemplary embodiments also provide a sterilization module having a structure capable of preventing leakage.

Additional features of the inventive concepts will be set forth in the description which follows, and in part will be apparent from the description, or may be learned by practice of the inventive concepts.

A sterilization module according to an exemplary embodiment includes a main body including an ultraviolet outlet, a transparent member disposed on the ultraviolet outlet and configured to transmit ultraviolet light, and a light source unit irradiating ultraviolet light toward the transparent member, and a sealing member, in which the light source unit includes a circuit board and a light emitting diode chip mounted on the circuit board, the light emitting diode chip including an epitaxial substrate, a conductive semiconductor layer formed on the epitaxial substrate, and an electrode, the conductive semiconductor layer of the light emitting diode chip is electrically connected to the circuit board directly by the electrode, ultraviolet light is configured to be irradiated toward the transparent member by passing through the epitaxial substrate, the sealing member forms a space, in which the light emitting diode chips is disposed, the sealing member being disposed between the transparent member and the circuit board, and a distance between the transparent member and the circuit board spaced apart from each other by the sealing member is greater than a height of the light emitting diode chip.

The electrode may be electrically connected to the circuit board, and may be bonded to the circuit board by a bonding material.

The bonding material may include a conductive material of at least one of silver (Ag), tin (Sn), or copper (Cu).

The sealing member may have a shape in which a top surface and a bottom surface are opened, and the sealing member may include a coupling groove disposed in an interior thereof to which the transparent member is to be inserted.

The sealing member may include a protrusion protruding from at least one of a top surface, a bottom surface, and a side surface of the sealing member.

The main body may include an upper body in which the ultraviolet outlet is formed and a lower body positioned under the upper body and providing a space in which the light source unit is to be installed, a top surface of the sealing member may be in close contact with a bottom surface of the upper body, and the upper body may include a seating part formed along a circumference of the ultraviolet outlet.

The upper body may have a bottom surface including a guide extending in a first direction and in close contact with a side surface of the sealing member, a length of the sealing member in the first direction may be greater than a length of the guide in the first direction.

The bottom surface of the upper body may include a main body coupling part extending in the first direction to fix the circuit board to the upper body, and a length of the main body coupling part in the first direction may be is equal to a length of the sealing member in the first direction.

The sterilization module may further include a fastening member penetrating the circuit board and coupled to the main body coupling part, when the fastening member is coupled to the main body coupling part, the fastening member may be configured to pressurize the circuit board, the circuit board may be configured to pressurize the sealing member, and the sealing member may be configured to be elastically reduced by the pressure between the seating part and the circuit board.

The fastening member may be a screw, and a screw groove may be formed on an inner wall of the main body coupling part.

The fastening member may include a hook to be coupled to the main body coupling part.

The circuit board may include a light source module coupling part through which the fastening member penetrates and a connecting passage for drawing a wire to supply power to the light source from an outside.

The sterilization module may further include a plurality of support members in close contact with a bottom surface of the upper body and a side surface of the lower body, in which at least one of the plurality of support members may be exposed to an outside through the connecting passage, the main body coupling part for fixing the circuit board to the upper body may be formed on a bottom surface of the upper body, and at least a part of a side surface of the guide may be in contact with the main body coupling part.

The main body may include an upper body in which the ultraviolet outlet is formed and a lower body positioned under the upper body and providing a space in which the light source unit is installed, in which the sealing member may include a first sealing member interposed between the upper body and the transparent member and a second sealing member interposed between the transparent member and the circuit board and different from the first sealing member.

The sterilization module may further include a connector mounted on the circuit board and electrically connected to the light source, in which a distance between the transparent member and the circuit board spaced apart from each other by the sealing member may be greater than a height of the connector.

A sterilization module according to another exemplary embodiment includes a main body including a through pipe having a first shape cross-section, a light source unit provided in the through pipe of the main body and having a second shape different from the first shape, a transparent member provided in an optical path of light emitted from the light source unit and sealing one side of the through pipe, a waterproof resin filled inside the main body and sealing the other end of the through pipe, and a sealing member provided inside the main body and sealing a gap between the through pipe and the light source unit, in which the light source unit includes a board having a first surface and a second surface and a light emitting diode disposed on the first surface of the board and configured to emit, the waterproof resin is provided on the second surface of the board, and the board has the second shape.

The waterproof resin and the transparent member may be spaced apart from each other with the board interposed therebetween.

The sterilization module may further include an outer holder coupled to the main body, in which the outer holder may include an outer holder coupling part configured to be coupled to an outer wall of a reservoir, and a size of a cross-section of the outer holder coupling part may be less than a size of a cross-section of the through pipe.

A sterilization module according to still another exemplary embodiment includes a main body including a through pipe, a light source unit provided inside the through pipe of the main body, a transparent member provided in an optical path of light emitted from the light source unit and sealing one side of the through pipe, and a waterproof resin filled inside the main body and sealing the other end of the through pipe, in which the light source unit includes a board having a first surface and a second surface and a light emitting diode disposed on the first surface of the board and configured to emit light, the board includes a wiring part, the light emitting diode is electrically connected to the wiring part of the board directly, the light emitting diode is provided in a form of a chip to emit light toward the transparent member directly without a lens and a case, and the waterproof resin is disposed on the second surface of the board.

The waterproof resin may be in contact with the second surface of the circuit board.

The sterilization module may further include an outer holder coupled to the main body, in which the outer holder may include an outer holder coupling part configured to be coupled to an outer wall of a reservoir, a size of a cross-section of the outer holder coupling part may be less than a size of a cross-section of the through pipe.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
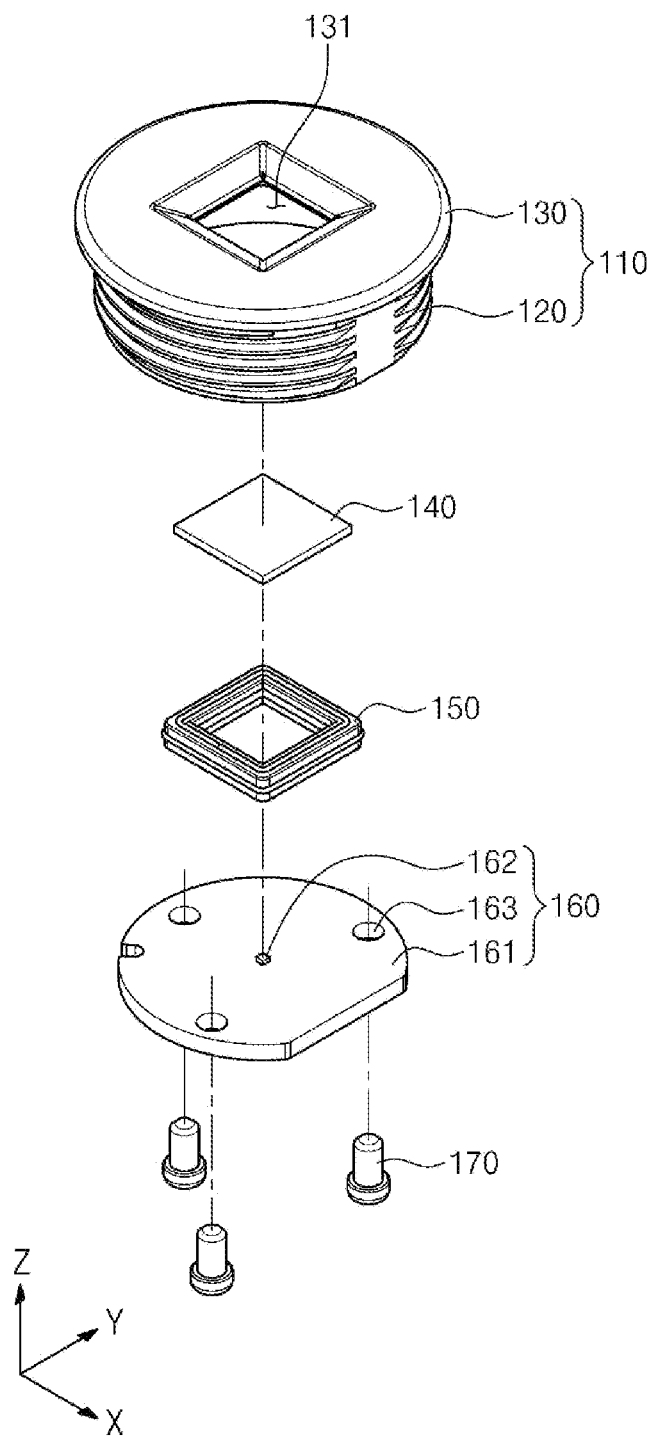
FIG. 1 is an exploded perspective view of a sterilization module according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
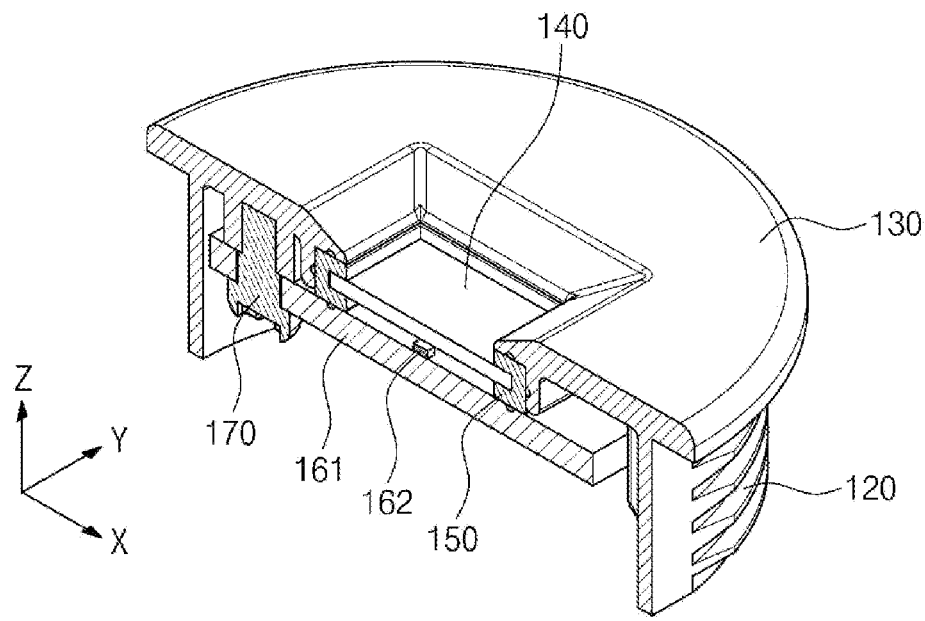
FIG. 2 is a perspective cross-sectional view illustrating a sterilization module according to an exemplary embodiment.

FIG. 1 is a perspective view illustrating a sterilization module according to an exemplary embodiment, and FIG. 2 is a cross-sectional view illustrating the sterilization module of FIG. 1 when assembled.

Referring to FIGS. 1 and 2, a sterilization module according to an exemplary embodiment includes a main body 110, a transparent member 140, a sealing member 150, a light source unit 160, and a fastening member 170.

The main body 110 has a structure, in which a part of the top surface and the bottom surface is opened, and forms the appearance of the sterilization module. The main body 110 also provides the space, in which the transparent member 140, the sealing member 150, the light source unit 160, or the like are installed. The main body 110 includes a lower body 120 and an upper body 130.

The lower body 120 is formed at the lower portion of the main body 110. The lower body 120 may be formed in the cylinder shape, in which the upper and lower surfaces are opened. However, the inventive concept are not limited thereto, and the shape of the lower body 120 is not particularly limited, as long as the sealing member 150 and the light source unit 160 may be mounted therein. For example, the lower body 120 may be formed in the shape of a polygon, such as a quadrangular shape. As another example, the outer side of the lower body 120 may be shaped in the form of a cylinder, and the inside of the lower body 120 may be formed in the shape of a polygon.

The upper body 130 is formed on the upper portion of the main body 110, and is formed to cover the lower body 120. The upper body 130 may be formed, such that the cross-section in the lateral direction, for example, in the first direction (e.g., X direction) and the second direction (e.g., Y direction) has a circular shape. However, the inventive concepts are not limited thereto, and the shape of the upper body 130 may be varied. For example, in some exemplary embodiments, the upper body 130 may be formed, such that the cross-section in the lateral direction has the shape of a polygonal, oval, or the like.

An UV outlet 131 is formed at the center of the upper body 130. The UV outlet 131 corresponds to a passage, through which UV emitted from the light source unit 160 is emitted to the outside of the sterilization module. The UV outlet 131 may be formed, for example, in a rectangular shape penetrating the upper body 130. However, the inventive concepts are not limited a particular shape of the UV outlet 131, as long as the UV outlet 131 is capable of providing a passage for UV to be emitted to the outside. For example, the UV outlet 131 may be formed in a shape of a circle, polygon, or the like, that penetrates a part of the upper body 130.

Figure 20:
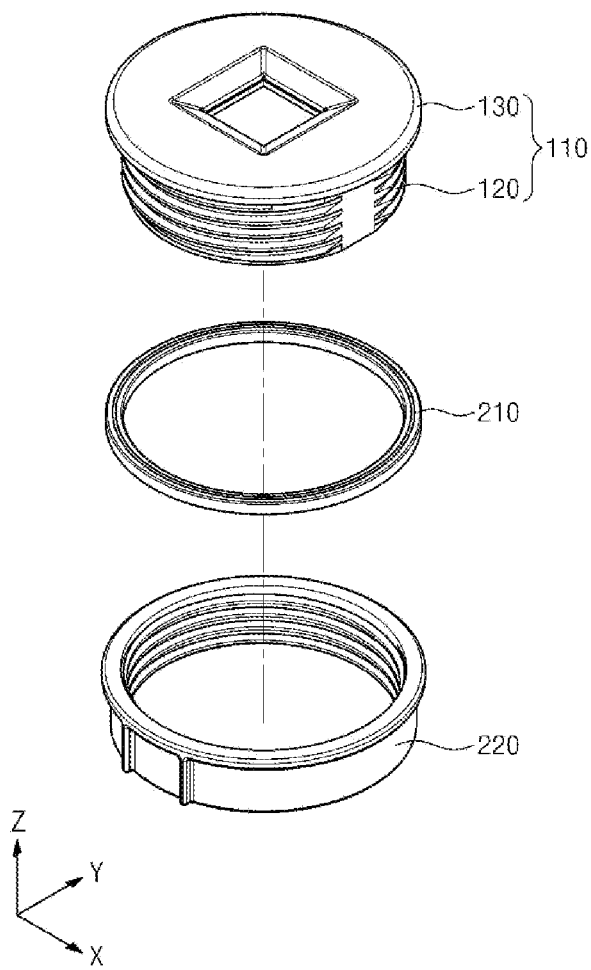
FIG. 20 is an exploded perspective view illustrating that an outer holder is coupled to the sterilization module of FIG. 1.

The sterilization module may be mounted in the external device by the screw combination with an outer holder 220 (refer to FIG. 20). In this case, as illustrated in FIG. 1, a screw thread that is to be screwed with the outer holder 220 (refer to FIG. 20) may be formed on the outer circumferential surface of the lower body 120. The diameter of the upper body 130 may be formed to be greater than the diameter of the lower body 120 to seat the outer holder 220. This will be described in more detail with reference to FIG. 17 below.

The transparent member 140 is formed to have a shape corresponding to the UV outlet 131. The transparent member 140 is installed in the UV outlet 131 together with the sealing member 150, so as to isolate the interior of the main body 110 from the exterior of the main body 110. For example, as illustrated in FIG. 1, when the UV outlet 131 has the shape of a rectangle, the transparent member 140 may be formed in a rectangular shape, similarly to the UV outlet 131. However, the inventive concepts are not limited to a particular shape of the transparent member 140, as long as the transparent member 140 is seated in the UV outlet 131 and may isolate the exterior and the interior of the main body 110 from each other.

The transparent member 140 is formed using a material that transmits UV, such that the UV emitted from the light source unit 160 is capable of being emitted to the outside of the sterilization module. For example, the transparent member 140 may be formed using at least one of quartz, fused silica, polymethyl methacrylate (PMMA) resin, and fluorinated polymer resin.

The sealing member 150 houses the transparent member 140 therein, and provides a waterproof structure between the UV outlet 131 and the transparent member 140. For example, as illustrated in FIG. 2, a coupling groove for accommodating each end of the transparent member 140 may be formed on the inner side surface of the sealing member 150. The transparent member 140 may be accommodated in the sealing member 150 by inserting the ends of the transparent member 140 into the coupling groove. Then, the sealing member 150 is installed in the UV outlet 131 together with the transparent member 140. A board 161 may pressurize the sealing member 150 to seal the space between the UV outlet 131 and the transparent member 140. As such, an external moisture or the like may be prevented from penetrating through the UV outlet 131.

The sealing member 150 may be formed using a soft material having elasticity or an adhesive material. For example, the sealing member 150 may be formed of, but is not limited to, VITON®, ethylene propylene (E.P.R), TEFLON®, or KALREZ®.

The light source unit 160 emits UV having the sterilization function. The UV emitted by the light source unit 160 is emitted to the outside of the sterilization module through the transparent member 140. The light source unit 160 includes the board 161, a light source 162, and a light source unit coupling part 163.

The board 161 has the shape corresponding to the lower body 120, and is installed inside the lower body 120. For example, when the lower body 120 is formed in a cylindrical shape, the board 161 may have a shape, in which a cross-sectional view thereof in the lateral direction is a circular. Furthermore, a part of the side of the board 161 may be cut to draw the wire connected to the light source 162 to the outside. However, the inventive concepts are not limited to a particular shape of the board 161, as long as the board 161 may be installed in the lower body 120 to pressurize the sealing member 150.

The board 161 is electrically connected to the light source 162, so as to provide the light source 162 with power supplied from the outside. For example, the board 161 may be a circuit board, a printed circuit board (PCB), a metal board, or a ceramic board. However, the inventive concepts are not limited thereto, as long as the board 161 is capable of being electrically connected to the light source 162. In addition, the type and the material of the board 161 are not particularly limited.

The light source 162 is mounted on the top surface of the board 161, and emits the UV having sterilization effect. For example, the light source 162 may be a light emitting diode chip that emits UV in a wavelength range of 200 nm to 280 nm, which is in the UVC area. However, the inventive concepts are not limited thereto a particular type and an emission wavelength of the light source 162, as long as the UV emitted from the light source 162 has a sterilization effect.

The light source 162 mainly emits light in the upper direction of the board 161. However, the light source 162 may have various beam angles, and may emit a part of light not only in the upper direction but also in the side direction of the light source 162 depending on the light source 162. As such, in some exemplary embodiments, an additional reflection member may be provided in at least a part of the board 161 to maximize light facing the upper portion. The form or material of the reflection member is not particularly limited, as long as the reflection member is capable of upwardly reflecting light. For example, the reflection member may be provided on the upper surface of the board 161 in the form of a reflective film, and an inorganic filler, of which the particle size is small, may be used as the reflective material. The inorganic filler may be, but is not limited to, barium sulfate, calcium sulfate, magnesium sulfate, barium carbonate, calcium carbonate, magnesium chloride, aluminum hydroxide, magnesium hydroxide, calcium hydroxide, titanium dioxide, alumina, silica, talc, zeolite, and the like.

The light source unit coupling part 163 is formed to penetrate the board 161, and the board 161 is fixed to the main body 110 by the fastening member 170. For example, as illustrated in FIG. 1, three light source unit coupling parts 163 may be formed on the board 161. However, the inventive concepts are not limited to a particular number of the light source unit coupling parts 163, as long as the board 161 is capable of being securely fixed to the main body 110.

The fastening member 170 penetrates the light source unit coupling part 163 to fix the board 161 to the main body 110. For example, the fastening member 170 may be coupled to a main body coupling part 133 (refer to FIG. 2) of the main body 110 by penetrating the light source unit coupling part 163. For example, the fastening member 170 may be a screw. In this case, a screw groove may be formed on the inner wall of the main body coupling part 133 (refer to FIG. 4).

As described with reference to FIGS. 1 and 2, the sterilization module according to an exemplary embodiment emits UV to the outside through the transparent member 140. Accordingly, the sterilization module may perform a sterilization operation on the outside.

In particular, the sterilization module according to an exemplary embodiment may be mounted with a light source in the form of a chip, rather than an LED package, on the board 161. In this manner, the chip may be protected from the outside by the transparent member 140. In particular, the sterilization module according to an exemplary embodiment may provide the light source 162, the main body 110, and the transparent member 140 in one package. As such, the sterilization module may be miniaturized by providing the light source 162, the main body 110, and the transparent member 140 in one package.

In general, a conventional sterilization module using LED as a light source includes the main body and a transparent member mounted on the upper surface of the main body. The board and the light source mounted on the board may be disposed under the transparent member. In particular, since the conventional sterilization module normally uses an LED package as a light source, the LED package is mounted on the board, rather than an LED chip. An LED package generally includes a package structure, such as a lens unit and a case, for protecting the LED chip and electrically connecting the LED chip to the outside. For example, the LED package may be a lamp-type LED package, a surface-mounted LED package, a COB LED packages, or the like.

In this case, assuming that the distance in the third direction 'z' between the LED package and the transparent member is "a", "a" needs to be at least greater than the length (e.g., the height of the package) of the LED package in the third direction. In addition, when a connector or the like is mounted on the board, the distance "a" between the LED package and the transparent member may become longer.

On the other hand, the sterilization module according to an exemplary embodiment mounts an LED chip, rather than an LED package, on the board 161. In this case, assuming that the distance in the third direction 'z' between the LED chip 162 and the transparent member 140 is "b", "b" may be shorter than "a" because the height of the LED chip 162 is lower than the height of the LED package. Accordingly, the sterilization module according to an exemplary embodiment facilitates miniaturization as compared to the conventional sterilization module.

Figure 3:
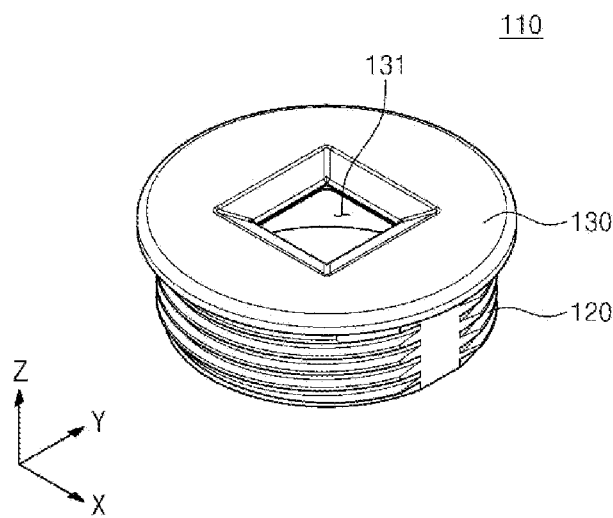
FIGS. 3 and 4 are perspective views illustrating shapes of the main body, respectively.
Figure 4:
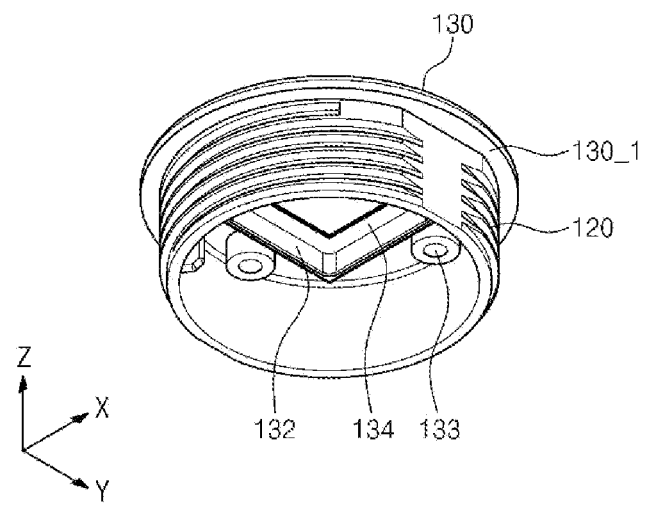
Figure 5:
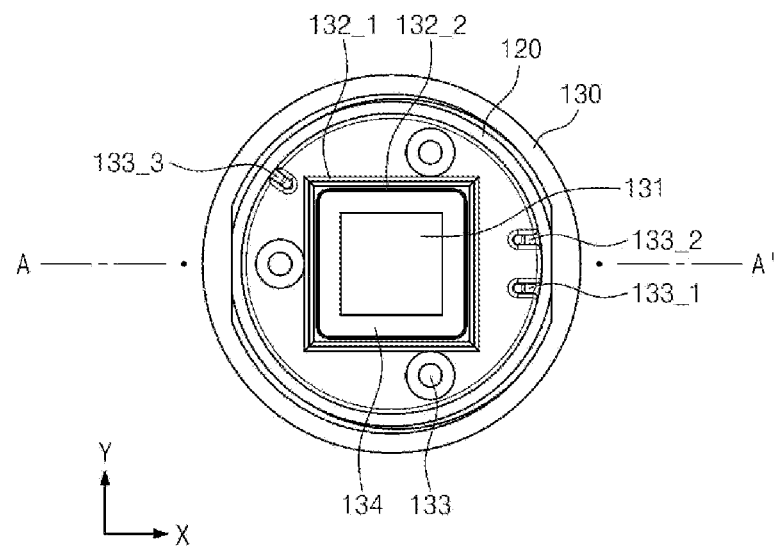
FIG. 5 is a bottom view illustrating a bottom surface of a main body.
Figure 6:
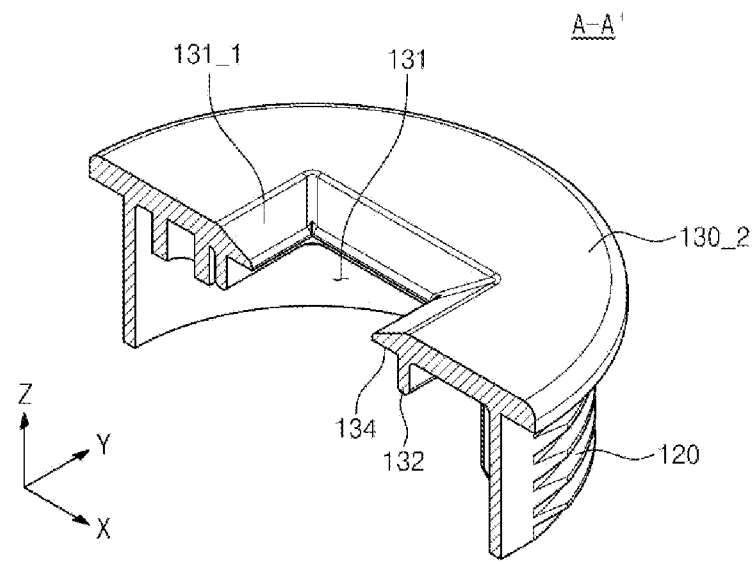
FIG. 6 is a perspective cross-sectional view of a main body.

FIGS. 3 to 6 are views illustrating the structure of the main body 110 of FIG. 1 in more detail. In particular, FIGS. 3 and 4 are perspective views illustrating the shapes of the main body 110, respectively, FIG. 5 is a bottom view illustrating the bottom surface of the main body 110, and FIG. 6 is a cross-sectional view of the main body 110.

Referring to FIGS. 3 to 6, the main body 110 may be divided into the upper body 130 and the lower body 120. The UV outlet 131, a guide 132, the main body coupling part 133, a seating part 134, and the like are formed in the upper body 130.

The UV outlet 131 is a passage, through which UV is emitted to the outside, and is formed to penetrate the upper body 130. An UV outlet sidewall 131_1 may be formed to have a predetermined slope, so as to minimize the loss of the UV emitted to the outside through the UV outlet 131.

In particular, when the UV emitted from the light source 162 is irradiated to the outside, a part of the UV may be reflected by the outlet sidewall 131_1 and may not be irradiated to the outside. In order to prevent such accidental reflection of UV, the UV outlet sidewall 131_1 may be formed to have a slope, in which the diameter of the inscribed circle increases from an upper body bottom surface 130_1 to an upper body top surface 130_2. In this case, the slope of the UV outlet sidewall 131_1 may be set to a range, in which UV is irradiated in the widest range, in consideration of the beam angle of the light source 162.

Furthermore, because the distance between the transparent member 140, which are installed in the UV outlet 131, and the light source 162 is formed shorter than that in the conventional sterilization module, the area of the UV outlet 131 may be formed to be smaller than that of the UV outlet of the conventional sterilization module.

In particular, when a light source with a constant beam angle is mounted in the sterilization module, the area of the transparent member 140 may need to be greater as the distance between the light source and the transparent member is increased, to emit UV to the outside through the transparent member 140 without the loss of UV. In this case, the UV outlet, where the transparent member is installed, also needs to be widened as the distance between the light source and the transparent member increases. In this manner, the miniaturization of the sterilization module may become difficult and its manufacturing cost may be increased. However, since the sterilization module according to an exemplary embodiment is mounted on the LED chip, rather than the LED package, on the board 161, the distance between the light source 162 and the transparent member 140 may become shorter than the conventional sterilization module. Accordingly, the UV outlet 131, in which the transparent member 140 is installed, may also be formed to be smaller than that of the conventional sterilization module.

The guide 132 is formed to protrude from the upper body bottom surface 130_1 in the third direction (e.g., Z direction). The guide 132 is also formed along the circumference of the UV outlet 131, and provides a space for accommodating the sealing member 150 together with the seating part 134.

The main body coupling part 133 is formed to protrude from the upper body bottom surface 130_1 in the third direction (e.g., Z direction). For example, as illustrated in FIG. 4, three main body coupling parts 133 may be formed. However, the number of main body coupling parts 133 is not limited thereto, as long as the board 161 may be stably fixed.

For example, the one end protruding in the third direction of the main body coupling part 133 may be formed to be longer than the one end protruding in the third direction of the guide 132. In this case, when the board 161 is fixed to the main body 110, one end of the main body coupling part 133 may be in close contact with the top of the board 161, and one end of the guide 132 may not be in close contact with the top of the board 161.

As another example, the one end protruding in the third direction of the main body coupling part 133 may be formed to be positioned on the same line as one end protruding in the third direction of the guide 132. Accordingly, when the board 161 is fixed to the main body 110, one end of the main body coupling part 133 and one end of the guide 132 may be in close contact with the top surface of the board 161.

In this case, the length of the main body coupling part 133 in the third direction and/or the length of the guide 132 in the third direction may be formed in consideration of the heights of the sealing member 150 and the light source 162. For example, the length of the main body coupling part 133 in the third direction may be formed to be shorter than the height of the sealing member 150, such that waterproofing is achieved by the elastic compression of the sealing member 150. In addition, for the purpose of protecting the light source 162 mounted on the board 161, the length of the main body coupling part 133 in the third direction is formed, such that the distance between the transparent member 140 and the board 161 is longer than the height of the light source 162. This will be described in more detail with reference to FIGS. 15 and 16 below.

The seating part 134 is formed on the upper body bottom surface 130_1, and is formed along the perimeter of the UV outlet 131. For example, referring to FIG. 5, the seating part 134 is disposed between the guide 132 and the UV outlet 131, which is formed on the upper body bottom surface 130_1 along the circumference of the UV outlet 131.

The seating part 134 has a shape corresponding to the sealing member 150. For example, the shape and width in the transverse direction (e.g., first and second direction) of the seating part 134 may be formed to be the same as or similar to the shape and width of the sealing member 150 in the transverse direction. As such, the sealing member 150 may not be directly exposed to the outside, and thus, may not harm the aesthetics of the sterilization module.

First to third support members 133_1 to 133_3 may be formed on the upper body bottom surface 130_1 and the inner side surface of the lower body 120. The first to third support members 133_1 to 133_3 support the lower body 120 more stably by dispersing the pressure applied to the lower body 120 to the upper body 130 when the outer holder 220 (refer to FIG. 20) is coupled.

The main body 110 may be formed of a waterproof material, or the outer wall of the main body 110 may be coated with a waterproof material. The outer wall of the main body 110 is a surface exposed to the outside of the main body 110. For example, the outer wall of the main body 110 may be the outer side surface of the lower body 120, the upper body top surface 130_2, and the upper body bottom surface 130_1. The outer wall of the main body 110 is coated with a waterproof material, thereby preventing the main body 110 from being corroded by moisture or the like. Also, the sterilization module may be prevented from degraded due to the corrosion by water.

Figure 7:
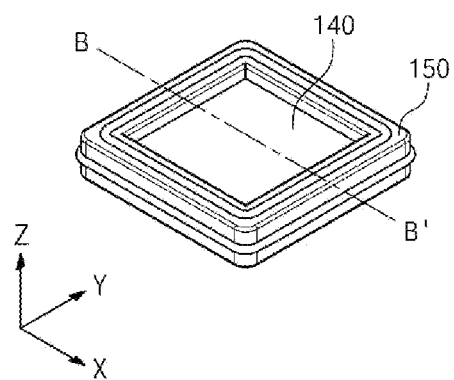
FIG. 7 is a perspective view illustrating a combination of a transparent member and a sealing member.
Figure 8:
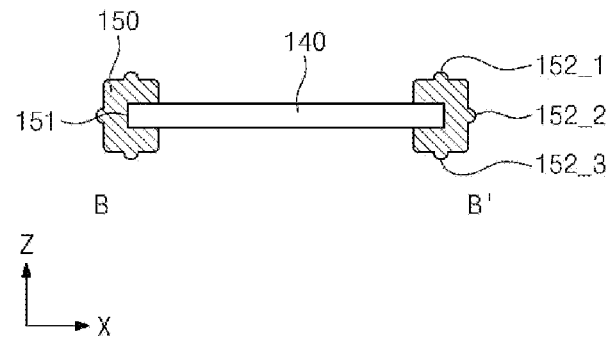
FIG. 8 is a cross-sectional view illustrating a combination of a transparent member and a sealing member.

FIGS. 7 and 8 illustrate the transparent member 140 and the sealing member 150 of FIG. 1. In particular, FIG. 7 is a perspective view illustrating a combination of the transparent member 140 and the sealing member 150, and FIG. 8 is a cross-sectional view illustrating a combination of the transparent member 140 and the sealing member 150.

Referring to FIGS. 7 and 8, a coupling groove 151 is formed inside the sealing member 150. Each end of the transparent member 140 is coupled to be inserted into the coupling groove 151 of the sealing member 150. Moreover, first to third protrusions 152_1 to 152_3 are formed along the circumference of the sealing member 150 on the top surface, the side surface, and the bottom surface of the sealing member 150, which may enhance waterproof features.

In particular, when the fastening member 170 is fastened to the main body coupling part 133 through the light source unit coupling part 163 of the board 161, the board 161 pressurizes the sealing member 150. In this case, the top surface of the sealing member 150 is pressed close to the seating part 134, the side surface of the sealing member 150 is close to the guide 132, and the bottom surface of the sealing member 150 is pressed close to the board 161.

At this time, when the pressure applied to the sealing member 150 by the board 161 is too high, the transparent member 140 may be damaged. Accordingly, the pressure applied to the sealing member 150 by the board 161 should not exceed a predetermined reference pressure. On the other hand, when the pressure applied to the sealing member 150 by the board 161 is too small, there may be a risk of not being waterproof.

As such, for the purpose of preventing such risk, the sealing member 150 may further include the first to third protrusions 152_1 to 152_3. Because the first to third protrusions 152_1 to 152_3 are formed in a narrow width, the first to third protrusions 152_1 to 152_3 may be deformed due to the elasticity thereof. Accordingly, the sealing member 150 may be easily compressed and then tightly fitted even at a small pressure. Accordingly, it is possible to improve the waterproofing ability without affecting the transparent member 140.

The surface of the transparent member 140 may be applied with a water repellent coating. When the surface of the transparent member 140 is applied with the water-repellent coating, the water drop may easily fall off the surface of the transparent member 140, because the water drop dropped to the transparent member 140 does not spread and clumps together. Accordingly, the amount of UV light emitted to the outside may not be decreased by the water droplets falling on the transparent member 140.

Furthermore, the surface of the sealing member 150 or the inner wall of the sealing member 150 may be coated with, for example, a material with high reflectivity, such as stainless steel, aluminum, magnesium oxide, Teflon®, or the like. In this case, the sealing member 150 may reflect UV hitting the inner wall of the sealing member 150, and then may allow the UV to face the UV outlet 131. Accordingly, the sterilization efficiency of the sterilization module may be improved by preventing the UV from being lost by hitting the inner wall of the sealing member 150.

Figure 9:
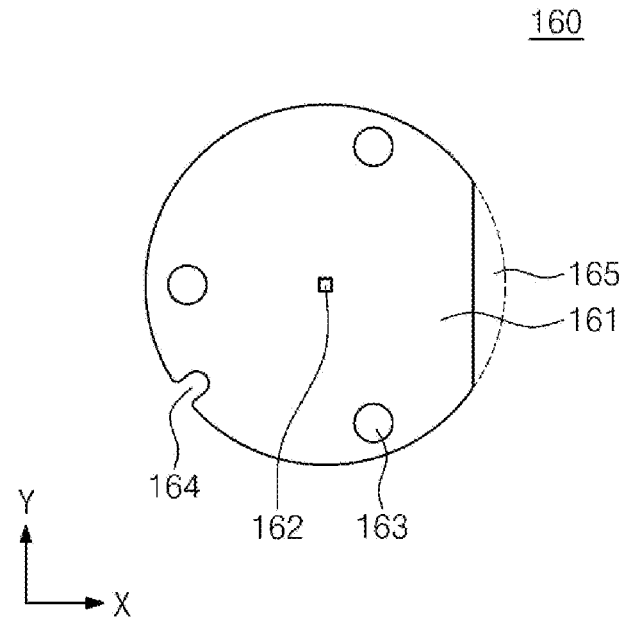
FIG. 9 is a view illustrating a light source mounted on a board.
Figure 10:
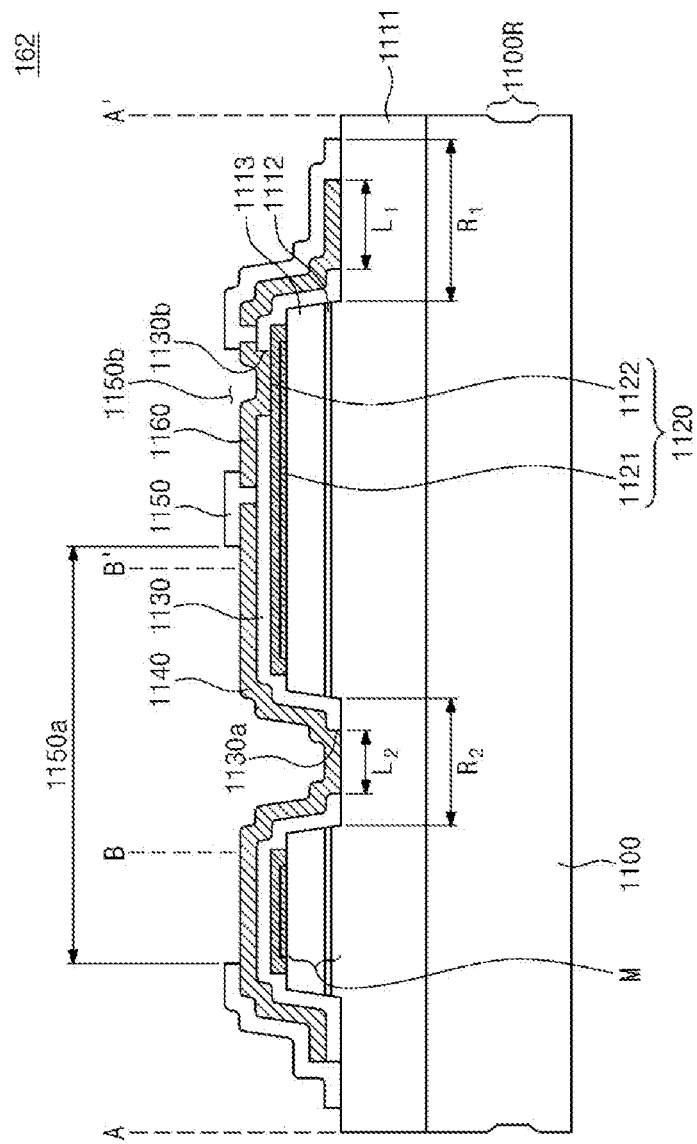
FIGS. 10 and 11 are cross-sectional views illustrating a structure of a light source.
Figure 11:
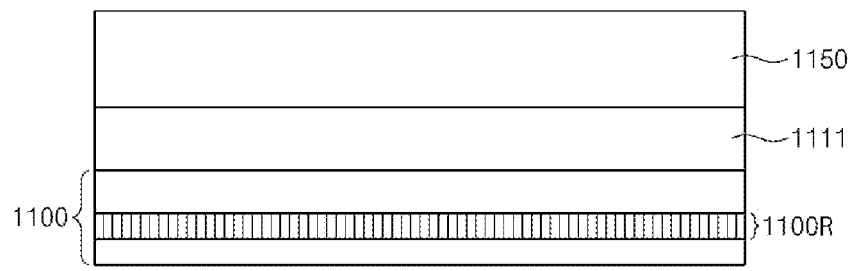

FIGS. 9 to 11 are views illustrating the light source unit 160 in more detail. In particular, FIG. 9 is a view illustrating that the light source 162 is mounted on the board 161, and FIGS. 10 and 11 are cross-sectional views illustrating the structure of the light source 162.

Referring to FIG. 9, the light source unit 160 includes the board 161, the light source 162, the light source unit coupling part 163, a support groove 164, and a connecting passage 165.

The light source 162 is mounted on the top surface of the board 161. The connecting passage 165 for drawing a wire for supplying power to the light source 162 to the outside is formed on one side of the board 161. The support groove 164 for passing through the third support member 133_3 (refer to FIG. 5), when the board 161 is fixed to the main body 110, is formed on the other side of the board 161.

The board 161 may be, but is not limited to, a heat dissipation board. As another example, the board 161 may be a printed circuit board.

The light source 162 is mounted on the top surface of the board 161, and emits the UV having sterilization effect. FIG. 9 shows that a single light source 162 is mounted on the upper surface of the board 161. However, the inventive concepts are not limited to a particular number of light sources 162 mounted on the board 161. For example, in some exemplary embodiments, a plurality of light sources 162 may be mounted on the upper surface of the board 161.

The light source unit coupling part 163 is formed to penetrate the board 161, and the board 161 is fixed to the main body 110 by the fastening member 170.

The light source 162 may be mounted on the board 161 in various ways. For example, the light source 162 may be an LED, and the LED may be formed by growing a conductive semiconductor layer, an active layer, and the like on an epitaxial substrate. Furthermore, when the LED is mounted on the board 161, the epitaxial substrate faces the transparent member 140 while being spaced from the board 161, and thus, the UV may be emitted through the epitaxial substrate. In this case, because the beam angle of the UV passing through the epitaxial substrate is greater than the beam angle of the UV not passing through the epitaxial substrate, a wider range may be sterilized effectively.

FIG. 10 illustrates a cross-sectional view of the light source 162 according to an exemplary embodiment, and FIG. 11 illustrates a cross-sectional view taken along line A-B-B'-A' of FIG. 10.

Referring to FIGS. 10 and 11, the light source 162 according to an exemplary embodiment may include a Mesa 'M' including a first conductive semiconductor layer 1111, an active layer 1112, and a second conductive semiconductor layer 1113, a first insulating layer 1130, a first electrode 1140, and a second insulating layer 1150. The light source 162 may further include an epitaxial substrate 1100 and a second electrode 1120.

The epitaxial substrate 1100 is not particularly limited as long as the epitaxial substrate 1100 may be capable of growing the first conductive semiconductor layer 1111, the active layer 1112, and the second conductive semiconductor layer 1113 thereon. For example, the epitaxial substrate 1100 may be a sapphire substrate, a silicon carbide substrate, a gallium nitride substrate, an aluminum nitride substrate, a silicon substrate, or the like. The side surface of the epitaxial substrate 1100 may include an inclined portion, thereby improving the extraction of light generated in the active layer 1112.

The second conductive semiconductor layer 1113 may be disposed on the first conductive semiconductor layer 1111. The active layer 1112 may be interposed between the first conductive semiconductor layer 1111 and the second conductive semiconductor layer 1113. The first conductive semiconductor layer 1111, the active layer 1112, and the second conductive semiconductor layer 1113 may include a III-V series compound semiconductor and may include, for example, a nitride-based semiconductors, such as Al, Ga, In N, and the like. The first conductive semiconductor layer 1111 may include n-type impurities (e.g., Si), and the second conductive semiconductor layer 1113 may include p-type impurities (e.g., Mg), or vice versa. The active layer 1112 may include a multi-quantum well structure (MQM). When forward bias is applied to the light source 162, the light source 162 emits light while electrons and holes are combined in the active layer 1112. The first conductive semiconductor layer 1111, the active layer 1112, and the second conductive semiconductor layer 1113 may be grown on the epitaxial substrate 1100 using technology, such as metalorganic chemical vapor deposition (MOCVD) or molecular beam epitaxy (MBE).

The light source 162 may include at least one Mesa 'M' including the active layer 1112 and the second conductive semiconductor layer 1113. The Mesa 'M' may include a plurality of protrusions, and the plurality of protrusions may be spaced from one another. The light source 162 may include, but is not limited to, a plurality of the Mesas 'M's spaced from one another. The side surface of the Mesa 'M' may be obliquely formed using the technology, such as photoresist reflow. The inclined side surface of the Mesa 'M' may improve the luminous efficiency generated in the active layer 1112.

The first conductive semiconductor layer 1111 may include a first contact area R1 and a second contact area R2, which are exposed through the Mesa 'M'. Because the Mesa 'M' is formed by removing the active layer 1112 and the second conductive semiconductor layer 1113 disposed on the first conductive semiconductor layer 1111, the portion other than the Mesa 'M' becomes a contact area, which may be the exposed top surface of the first conductive semiconductor layer 1111. The first electrode 1140 may be electrically connected to the first conductive semiconductor layer 1111 by contacting the first contact area R1 and the second contact area R2. The first contact area R1 may be disposed around the Mesa 'M' along the outer portion of the first conductive semiconductor layer 1111. In particular, the first contact area R1 may be disposed between the Mesa 'M' and the side surface of the light source 162 along the outer portion on the upper surface of the first conductive semiconductor layer 1111. The second contact area R2 may be at least partially surrounded by the Mesa 'M'.

The length of the second contact area R2 in the long axis direction may be not less than about 0.5 times the length of one side of the light source 162. In this manner, the area in which the first electrode 1140 and the first conductive semiconductor layer 1111 contacts each other may be increased, and the current flowing from the first electrode 1140 to the first conductive semiconductor layer 1111 may be more effectively distributed, thereby further reducing the forward voltage.

The second electrode 1120 is disposed on the second conductive semiconductor layer 1113, and may be electrically connected to the second conductive semiconductor layer 1113. The second electrode 1120 is formed on the Mesa 'M' and may have substantially the same shape depending on the shape of the Mesa 'M'. The second electrode 1120 may include a reflective metal layer 1121, and may further include a barrier metal layer 1122. The barrier metal layer 1122 may cover the top and side surfaces of the reflective metal layer 1121. For example, the barrier metal layer 1122 may be formed to cover the top and side surfaces of the reflective metal layer 1121 by forming a pattern of the reflective metal layer 1121 and forming the barrier metal layer 1122 on the reflective metal layer 1121. For example, the reflective metal layer 1121 may be formed by depositing and patterning Ag, an alloy thereof, Ni/Ag, NiZn/Ag, or TiO/Ag layer.

The barrier metal layer 1122 may be formed of Ni, Cr, Ti, Pt, Au, or a composite layer thereof. In particular, the barrier metal layer 1122 may be the composite layer sequentially formed of Ni/Ag/[Ni/Ti]2/Au/Ti on the second conductive semiconductor layer 1113. More particularly, at least part of the upper surface of the second electrode 1120 may include a Ti layer having a thickness of about 300 Å. When the area contacting the first insulating layer 1130 in the upper surface of the second electrode 1120 is formed of the Ti layer, the adhesion between the first insulating layer 1130 and the second electrode 1120 may be improved, thereby improving the reliability of the light source 162.

An electrode protective layer 1160 may be disposed on the second electrode 1120, and the electrode protective layer 1160 may be formed of substantially the same material as the first electrode 1140, but is not limited thereto.

The first insulating layer 1130 may be interposed between the first electrode 1140 and the Mesa 'M'. The first electrode 1140 and the Mesa 'M' may be insulated through the first insulating layer 1130, and the first electrode 1140 and the second electrode 1120 may be insulated through the first insulating layer 1130. The first insulating layer 1130 may partially expose the first contact area R1 and the second contact area R2. In particular, the first insulating layer 1130 may expose a part of the second contact area R2 through an opening 1130a. In this case, since the first insulating layer 1130 covers only a part of the first contact area R1 between the outer portion of the first conductive semiconductor layer 1111 and the Mesa 'M', at least part of the first contact area R1 may be exposed.

The first insulating layer 1130 may be disposed on the second contact area R2 along the outer portion of the second contact area R2. In this case, the first insulating layer 1130 may be restrictively disposed closer to the Mesa 'M' than the area where the first contact area R1 and the first electrode 1140 contact each other.

The first insulating layer 1130 may have an opening 1130b exposing the second electrode 1120. The second electrode 1120 may be electrically connected to a pad, a bump, or the like through the opening 1130b.

The area where the first contact area R1 and the first electrode 1140 contact each other is disposed along the outer portion of the upper surface of the first conductive semiconductor layer. More particularly, the area where the first contact area R1 and the first electrode 1140 contact each other may be disposed adjacent to all four side surfaces of the first conductive semiconductor layer 1111, and may completely surround the Mesa 'M'. In this manner, because the area in which the first electrode 1140 and the first conductive semiconductor layer 1111 contacts each other may be increased, the current flowing from the first electrode 1140 to the first conductive semiconductor layer 1111 may be more effectively distributed, thereby further reducing the forward voltage.

According to an exemplary embodiment, the first and second electrodes 1140 and 1120 of the light source 162 may be mounted on the board 161, directly or via pads.

For example, when the light source 162 is mounted on the board 161 via a pad, two pads interposed between the light source 162 and the board 161 may be provided. The two pads may be in contact with the first electrode 1140 and the second electrode 1120, respectively. For example, the pad may be, but is not limited to, a solder or eutectic metal, such as AuSn.

As another example, when the light source 162 is mounted directly on the board 161, the first electrode 1140 and second electrode 1120 of the light source 162 may be directly bonded to the wire on the board 161. In this case, the bonding material may include an adhesive material having conductive properties. For example, the bonding material may include a conductive material of at least one of Silver (Ag), Tin (Sn), or Copper (Cu). However, the inventive concepts are not limited thereto, and the bonding material may include various other materials having conductivity.

Figure 12:
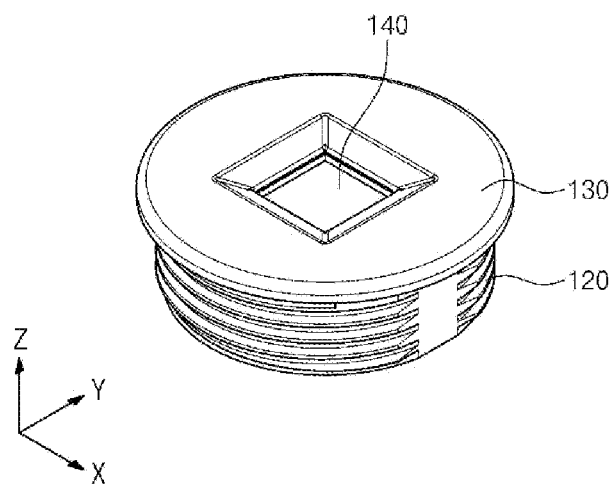
FIGS. 12 and 13 are perspective views illustrating that the sterilization module of FIG. 1 is assembled.
Figure 13:
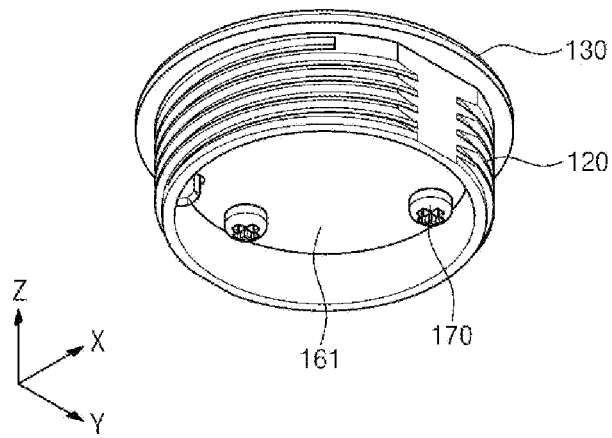
Figure 14:
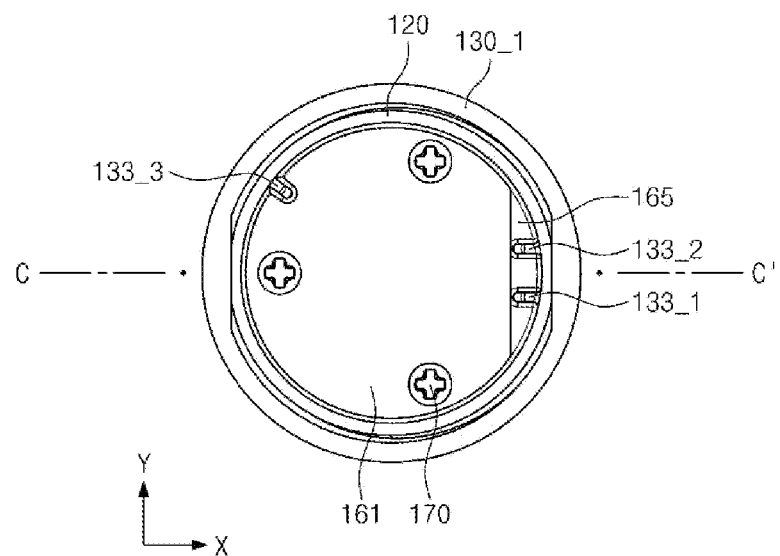
FIG. 14 is a bottom view illustrating that the sterilization module of FIG. 1 is assembled.
Figure 15:
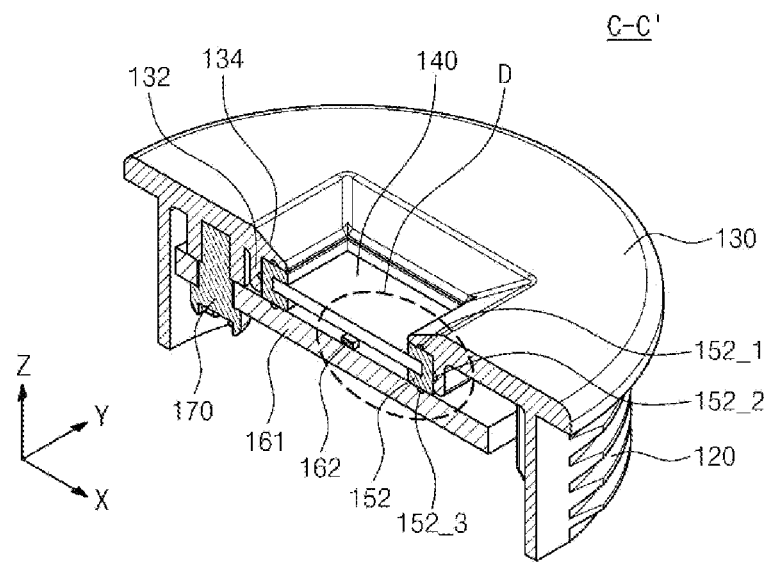
FIG. 15 is a perspective cross-sectional view taken along line C-C' of FIG. 14.
Figure 16:
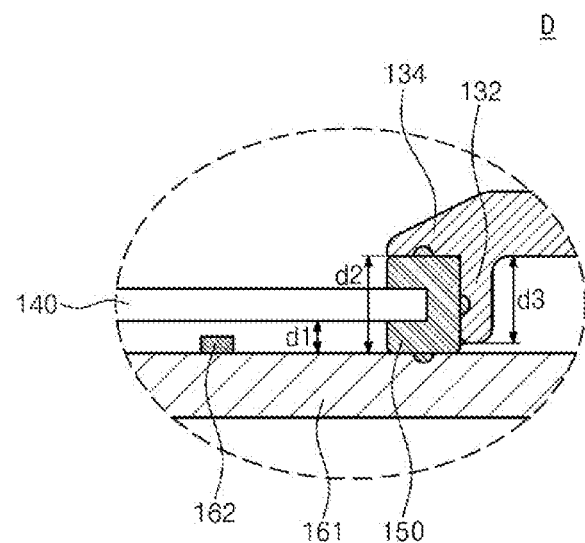
FIG. 16 is a partial enlarged view of portion D of FIG. 15.

FIGS. 12 to 16 are views illustrating that the sterilization module of FIG. 1 is assembled. In particular, FIGS. 12 and 13 are perspective views illustrating that the sterilization module of FIG. 1 is assembled, FIG. 14 is a bottom view illustrating that the sterilization module of FIG. 1 is assembled. FIG. 15 is a cross-section view taken along line C-C' of FIG. 14, and FIG. 16 is a partial enlarged view of portion D of FIG. 15.

Referring to FIGS. 12 to 14, the transparent member 140 is exposed to the outside through the UV outlet 131 formed on the top surface of the upper body 130. The fastening member 170 is fastened to the lower body 120 through the light source unit coupling part 163 formed on the board 161, and then fixes the board 161 to the lower body 120. In this case, the first and second support members 133_1 and 133_2 formed on the upper body bottom surface 130_1 are exposed to the outside through the connecting passage 165, and the third support member 133_3 is exposed to the outside through the support groove 164.

Referring to FIGS. 15 and 16, the fastening member 170 penetrates the board 161 to be fastened to the main body coupling part 133. In this case, the top surface of the board 161 is in close contact with the sealing member 150. The fastening member 170 may then pressurize the board 161 in the third direction (e.g., Z direction), and the board 161 may pressurize the sealing member 150. As the board 161 pressurizes the sealing member 150, the sealing member 150 is elastically compressed between the seating part 134 and the board 161. In this case, for example, the sealing member 150 that is elastically compressed by the pressure of the board 161 may have the length d2 in the third direction, which may be substantially the same as the length of the main body coupling part 133 in the third direction.

The sealing member 150 forms a predetermined spaced distance between the transparent member 140 and the board 161, such that the light source 162 mounted on the board 161 is not damaged, as well as preventing external moisture from penetrating into the sterilization module.

In particular, the penetration of moisture between the sealing member 150 and the seating part 134, between the sealing member 150 and the guide 132, and/or between the sealing member 150 and the board 161 may be prevented by elastic compression of the sealing member 150.

In addition, a predetermined spaced distance d1 may be formed between the transparent member 140 and the board 161 by the sealing member 150, which is inserted into opposite ends of the transparent member 140. The sealing member 150 may function as a spacer that physically separates the transparent member 140 and the board 161, such that the light source 162 is not damaged.

According to an exemplary embodiment, the distance d1 between the transparent member 140 and the board 161 is greater than the height of the light source 162 so as to protect the light source 162. In this case, the distance between the transparent member 140 and the light source 162 may be minimized to maximize sterilization power. For example, the distance d1 between the transparent member 140 and the board 161 may be set to be greater than or equal to about 200 μm and less than or equal to about 2 mm. The minimum distance d1 between the transparent member 140 and the board 161 takes into account the height of the light source 162 on the board 161. When the distance d1 between the transparent member 140 and the board 161 is less than about 200 μm, the light source 162 may be directly contacted by the transparent member 140 or may be pressed by the transparent member 140. However, the minimum distance d1 between the transparent member 140 and the board 161 may be set differently to have a value greater or smaller depending on the height of the light source 162. The maximum distance d1 between the transparent member 140 and the board 161 takes into account the sterilization power due to the UV. As the distance from the light source 162 increases, the intensity of the UV decreases significantly. For example, when the distance d1 between the transparent member 140 and the board 161 exceeds about 2 mm, there is little effect of sufficient sterilization by the UV. As such, the distance d1 between the transparent member 140 and the board 161 according to an exemplary embodiment may be 2 mm or less to sufficiently maintain sterilization power for the external fluid.

In a conventional sterilization module, an LED package is generally mounted on a board, and an LED chip is embedded in the LED package. Accordingly, the distance between the LED chip and the transparent member needs to be at least greater than the height of the LED package, which may reduce sterilization power depending on the increase in a distance. On the other hand, in the sterilization module according to an exemplary embodiment, because the LED chip is mounted on the board 161, rather than an LED package, the distance d1 between the light source 162 and the transparent member 140 may be shorter than the of the conventional sterilization module. In addition, because the transparent member 140 is separated from the board 161 using the sealing member 150 without a separate spacer, the distance d1 between the light source 162 and the transparent member 140 may be minimized. Accordingly, the sterilization module according to an exemplary embodiment may maximize the sterilization power.

Also, in the sterilization module according to an exemplary embodiment, because only one air layer is present between the transparent member 140 and the light source 162, heat dissipation performance is improved.

In particular, in a conventional sterilization module that includes an LED package mounted on a board, a double air layer is formed between an LED chip and a transparent member. For example, a first air layer may be formed inside the LED package, and a second air layer may be formed between the LED package and the transparent member. In this case, even though the transparent member may be in contact with an external cold fluid, it may be difficult to transmit the temperature of the fluid to the first air layer, due to the thermal insulation function of the second air layer. Accordingly, the cooling efficiency of the LED chip by the fluid may be reduced, which may degrade the LED chip and shorten the lifespan of the LED chip. On the other hand, in the sterilization module according to an exemplary embodiment, because the LED chip is mounted on the board 161, only one air layer is formed between the light source 162 and the transparent member 140. In this case, when the transparent member 140 is in contact with an external cold fluid, the heat dissipation performance of the sterilization module may be improved because the temperature of the air layer where the light source 162 is exposed decreases, thereby preventing the deterioration of a chip. In addition, because the LED chip in the sterilization module according to an exemplary embodiment directly contacts with the board 161 that has a heat dissipation function, the heat dissipation function may be further improved as compared to the conventional sterilization module.

The distance d1 between the transparent member 140 and the board 161 may be formed in proportion to the thickness of the sealing member 150. However, as described above, the thickness of the sealing member 150 may be greater than the thickness of the light source 162 to protect the light source 162. As such, the distance between the transparent member 140 and the light source 162 may be minimized to maximize the sterilization power. However, the inventive concepts are not limited thereto, and the thickness of the sealing member 150 may be variously adjusted as long as the sterilization module is waterproof.

In FIGS. 15 and 16, the length d3 of the guide 132 in the third direction is illustrated as being shorter than the length d2 of the main body coupling part 133 in the third direction. However, the inventive concepts are not limited thereto. For example, the length d3 of the guide 132 in the third direction may be formed to be the same as the length d2 of the main body coupling part 133 in the third direction. In this case, the board 161 may be in close contact with one end of the guide 132 and may be fixed more firmly. As such, the waterproof function may be further improved by the close contact between the board 161 and the guide 132.

According to an exemplary embodiment, the sterilization module may have a unique fastening structure to improve the waterproof function.

Figure 17A:
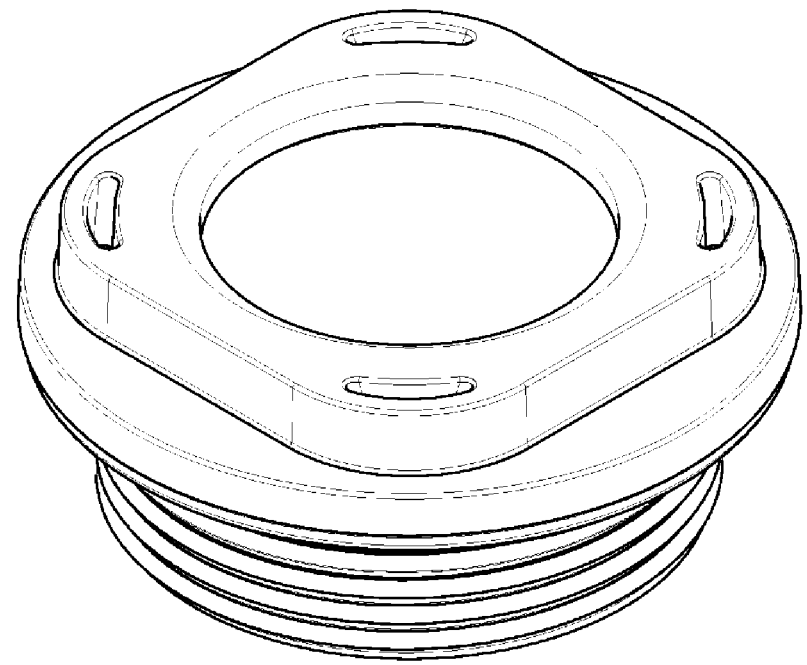
FIG. 17A is a schematic view of a sterilization module according to an exemplary embodiment.
Figure 17B:
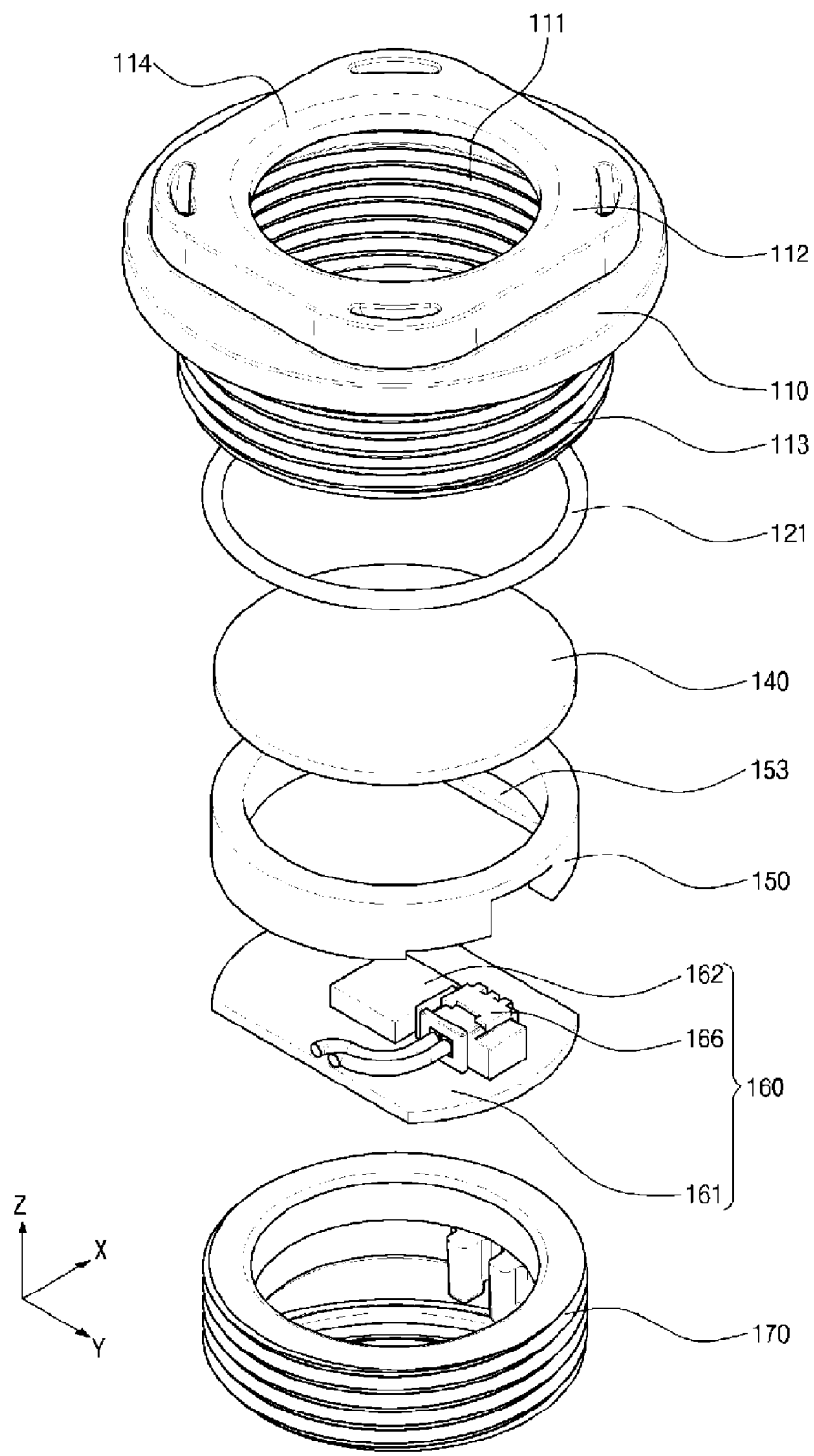
FIG. 17B is an exploded perspective view of a sterilization module according to an exemplary embodiment.

FIG. 17A is a cross-sectional view of a sterilization module according to an exemplary embodiment, and FIG. 17B is an exploded perspective view of a sterilization module according to an exemplary embodiment.

The sterilization module of FIGS. 17A and 17B includes the main body 110, the transparent member 140, the sealing member 150, and the light source unit 160. In addition, a waterproof resin is filled in the main body 110. The details of the filling type of the waterproof resin will be described in more detail with reference to FIG. 19.

The main body 110 includes a through pipe 111. The through pipe 111 extends in the length direction (e.g., z-axis direction) of the main body 110. The main body 110 has a shape opened in the length direction by the through pipe 111.

The main body 110 may have a length along the z-axis direction capable of maximally securing the irradiation angle of light emitted from the light source, for example, the light source 162, provided inside the main body 110. In particular, the main body 110 may have an extended shape, such that there is no loss of the irradiation angle by a connector 166.

FIG. 17B shows that the through pipe 111 has a circular cross-section. However, the shape of the through pipe 111 is not limited thereto. For example, in some exemplary embodiments, the through pipe 111 may have various other shapes, such as a square, a rectangle, a trapezoid, a rhombus, a triangle, an oval, a semicircle, a semi-ellipse, or the like, in addition to the circular shape.

A photocatalyst may be applied to the inner side surface of the through pipe 111. When UV is irradiated on the photocatalyst, sterilization materials, such as hydroperoxide ($H_2O_2$), hydroxyl, and hydroperoxyl radical may be emitted. These sterilization materials may damage the DNA, proteins, and fats inside a virus or bacteria to inactivate the virus or the bacteria.

The photocatalyst is applied to the inner side surface of the through pipe 111, and may be irradiated with light emitted from the light source unit 160. The photocatalyst may react to the light, and generate the sterilization material. Accordingly, the inner side surface of the through pipe 111 may be disinfected. The sterilization module according to an exemplary embodiment may be installed in a high humidity environment, such as a refrigerator, a washing machine, a humidifier, an air conditioner, a water purifier, or the like. The inside of the sterilization module may be easily contaminated because a virus grows actively in an environment with high humidity. Accordingly, even though the sterilization module is used continuously, it is possible to prevent the sterilization module from being contaminated by the virus by applying the photocatalyst to the inside of the sterilization module, in particular, the inner side surface of the through pipe 111.

The photocatalyst applied to the inner side surface of the through pipe 111 may include at least one selected from titanium oxide ($TiO_2$), zinc oxide (ZnO), cadmium sulfide (CdS), zirconium oxide ($ZrO_2$), vanadium oxide ($V_2O_3$), tungsten oxide ($WO_3$), and the combination thereof.

However, in some exemplary embodiments, the photocatalyst may be applied to various other portions of the through pipe 111. For example, the photocatalyst may also be applied to the exterior of the main body 110, the transparent member 140, or the like.

A screw thread 113 may be provided on one side of the main body 110. The screw thread 113 may be used to fasten the main body 110 to other structures. For example, the main body 110 may be fastened to an auxiliary body or may be fastened to a reservoir, in which the sterilization module is installed. For example, the other components fastened to the main body 110 may have a screw thread corresponding to the screw thread 113 of the main body 110.

In the case of using a screw-type fastening structure, a plurality of screw threads 113 may bear the stress applied to the sterilization module or the main body 110, thereby improving fastening strength. In addition, the screw thread 113 may allow a user to install the sterilization module in the reservoir or the like without an additional equipment, thereby improving user convenience.

In some exemplary embodiments, a waterproof tape may be further provided on the screw thread 113 to improve the waterproof structure. The waterproof tape may be Teflon® (PTFE), polyethyl terephthalate (PET), acrylic resin, urethane resin, polyvinyl chloride (PVC), or the like. The waterproof tape may be relatively thin and elastic, and thus, may be in close contact with the screw thread 113. As such, when the screw thread 113 of the main body 110 is coupled to the corresponding screw thread, the waterproof tape may fill the space between the two screw threads, and thus, water or the like may be prevented from penetrating between the screw threads.

However, the inventive concepts are not limited to the screw thread 113 for fastening the main body 110. For example, in some exemplary embodiments, the main body 110 may be fastened to an auxiliary body or a reservoir using various methods known in the art without the screw thread 113.

Referring to FIG. 17B, the main body 110 may include a protrusion part 112 protruding in the z-axis direction. The protrusion part 112 may have a different shape from the cross-section of the through pipe 111. For example, when the cross-section of the through pipe 111 is circular, the protrusion part 112 may be a rounded rectangle. The protrusion part 112 may protect the transparent member 140 from external impact. In some exemplary embodiments, the protrusion part 112 may be omitted.

In addition, the protrusion part 112 may function as a portion held by the user, when the user installs the sterilization module in a reservoir or the like. The user may easily install the sterilization module in the reservoir by screwing the sterilization module while holding the protrusion part 112.

The protrusion part 112 may have a height that may not cause the connector 166 of the light source unit 160 to contact the main body 110. Accordingly, even though the connector 166 is provided on the same side as the light source 162, the connector 166 may not be damaged by the main body 110.

The end of the protrusion part 114 may have an inclined shape. In particular, the end of the protrusion part 114 may have a slope in the form of spreading toward the end. As such, light emitted from the light source 162 toward the inside of the through pipe 111 may spread more widely along the slope of the end of the protrusion part 114. As such, the irradiation angle of the sterilization module may be larger and light may be irradiated to the larger region of the reservoir.

The transparent member 140 seals one side of the through pipe 111 of the main body 110, thereby preventing moisture from penetrating into the sterilization module through the through pipe 111. To this end, the transparent member 140 may have a shape corresponding to the cross-section of the through pipe 111 of the main body 110. For example, as illustrated in FIG. 17B, when the cross-section of the through pipe 111 is circular, the transparent member 140 may also be circular. However, the inventive concepts are not limited thereto, and the shape of the transparent member 140 may be varied depending on the cross-section of the through pipe 111. For example, the transparent member 140 may have various shapes, such as a square, a rectangle, a trapezoid, a rhombus, a triangle, an oval, a semicircle, a semi-ellipse, and the like in addition to the circle so as to correspond to the cross-section of the through pipe 111.

The transparent member 140 is substantially the same as that described above, and thus, repeated descriptions thereof will be omitted.

An inner sealing member 121 may be provided between the transparent member 140 and the main body 110. The inner sealing member 121 may fill the empty space between the transparent member 140 and the main body 110. The inner sealing member 121 may be made of an elastic material, and may have a diameter slightly greater than the diameter of the through pipe 111.

The inner sealing member 121 having a diameter slightly greater than the diameter of the through pipe 111 may be compressed, and then may be inserted into the through pipe 111 of the main body 110 in the compressed state. The inserted inner sealing member 121 expands in the through pipe 111 because the inserted inner sealing member 121 is elastic. Accordingly, the through pipe 111 and the inner sealing member 121 may be in close contact with each other. After inserting the inner sealing member 121, the transparent member 140 may be provided to the through pipe 111. The transparent member 140 may be pushed in the z-axis direction by the sealing member 150 or the like, and may be in close contact with the inner sealing member 121. As such, the empty space between the main body 110 and the transparent member 140 may be removed, and the sterilization module may be watertight.

The inner sealing member 121 not only prevents moisture from penetrating into the sterilization module, but also may function as a buffer between the main body 110 and the transparent member 140. Accordingly, a shock applied to the main body 110 may be buffered, and then may be transmitted to the transparent member 140. As such, even when the transparent member 140 is manufactured using a relatively low impact material, such as glass, the breakage of the transparent member 140 may be prevented.

The inner sealing member 121 may be formed of, but is not limited to, VITON®, ethylene propylene (E.P.R), TEFLON®, or KALREZ®.

The sealing member 150 may be provided on the transparent member 140. The sealing member 150 shown in FIG. 1 surrounds the transparent member 140, however, the sealing member 150 according to the illustrated exemplary embodiment may be provided in the form of pressurizing the transparent member 140 on one side.

Furthermore, according to an exemplary embodiment, the sealing member 150 includes an open part having a shape different from the through pipe 111. In this case, the shape of the open part of the sealing member 150 may refer to the shape of the opening other than a region obscured by the sealing member 150. A region obscured by the sealing member 150 includes the region obscured by a wing 153 included in the sealing member 150.

The sealing member 150 has the wing 153, which is provided integrally with the sealing member 150 in the interior of the sealing member 150. The open part shape of the sealing member 150 differs from the shape of the cross-section of the through pipe 111 by the wing 153.

For example, when the exterior appearance of the sealing member 150 has a circular shape, and when the wing 153 protrudes from the inside of the sealing member 150 like a string provided in a circle, the open part shape of the sealing member 150 may be is a rectangular with two opposite arcs, other than the region obscured by the wing 153.

The shape of the open part of the sealing member 150 corresponds to the shape of the board 161 of the light source unit 160.

The diameter of the sealing member 150 may be similar to the diameter of the transparent member 140. Accordingly, the sealing member 150 may push the transparent member 140 in the z-axis direction on the bottom surface of the transparent member 140. As such, as described above, the transparent member 140 and the main body 110 or the inner sealing member 121 may be in close contact with each other.

In addition, the sealing member 150 may have a shape that corresponds to the shape of the cross-section of the through pipe 111 of the main body 110. For example, when the shape of the cross-section of the through pipe 111 is a circle, the sealing member 150 may have a circular shape. The sealing member 150 may have various shapes, such as a square, a rectangle, a trapezoid, a rhombus, a triangle, an oval, a semicircle, a semi-ellipse and the like in addition to the circle, so as to correspond to the cross-section of the through pipe 111.

The sealing member 150 may not need to be in close contact with the inner side surface of the through pipe 111. However, the sealing member 150 may be in close contact with the through pipe 111, such that the sealing member 150 and the light source unit 160 in close contact with each other are fixed within the main body 110. In this case, the sealing member 150 and the through pipe 111 may not need to be in close contact with each other so as to be watertight.

In some exemplary embodiments, a screw thread may be provided on the sealing member 150. The screw thread provided to the sealing member 150 may correspond to the screw thread provided to the inner side surface of the through pipe 111. As such, the sealing member 150 may be screwed in to the main body 110. In this manner, the sealing member 150 and the through pipe 111 may be in close contact with each other. As such, the sealing member 150 may be more stably fixed in the main body 110, thereby improving the structural stability of the sterilization module. Moreover, a user may further push the sealing member 150 in the z-axis direction along the screw thread of the sealing member 150, thereby further strengthening the watertight structure between the inner sealing member 121 and the transparent member 140.

In addition, the sealing member 150 may be coupled to the main body 110, in the hook scheme or in the scheme, in which the sealing member 150 is formed of an elastic ring having elasticity and then is fixed, in addition to the scheme of fixing the sealing member 150 using a screw.

The sealing member 150 may function as a spacer that separates the board 161 of the light source unit 160 from the transparent member 140. Accordingly, the thickness of the sealing member 150 in the z-axis direction may be set to minimize the loss of the amount of light emitted from the light source unit 160. Accordingly, according to an exemplary embodiment, the thickness of the sealing member 150 in the z-axis direction may be in a range of about 200 µm to about 2 mm. However, the inventive concepts are not limited thereto, and in some exemplary embodiments, the distance between the transparent member 140 and the board 161 may be at least about 2 mm.

The thickness of the wing 153 may be less than the thickness of the sealing member 150. Accordingly, the wing 153 has a shape protruding from the inside of the sealing member 150. A location where the wing 153 is provided inside the sealing member 150 is not particularly limited. The wing 153 may be provided integrally with the bottom surface of the sealing member 150.

The light source unit 160 may be provided on the sealing member 150. The light source unit 160 may include the light source 162, the connector 166, a wiring part, and the board 161.

Figure 17C:
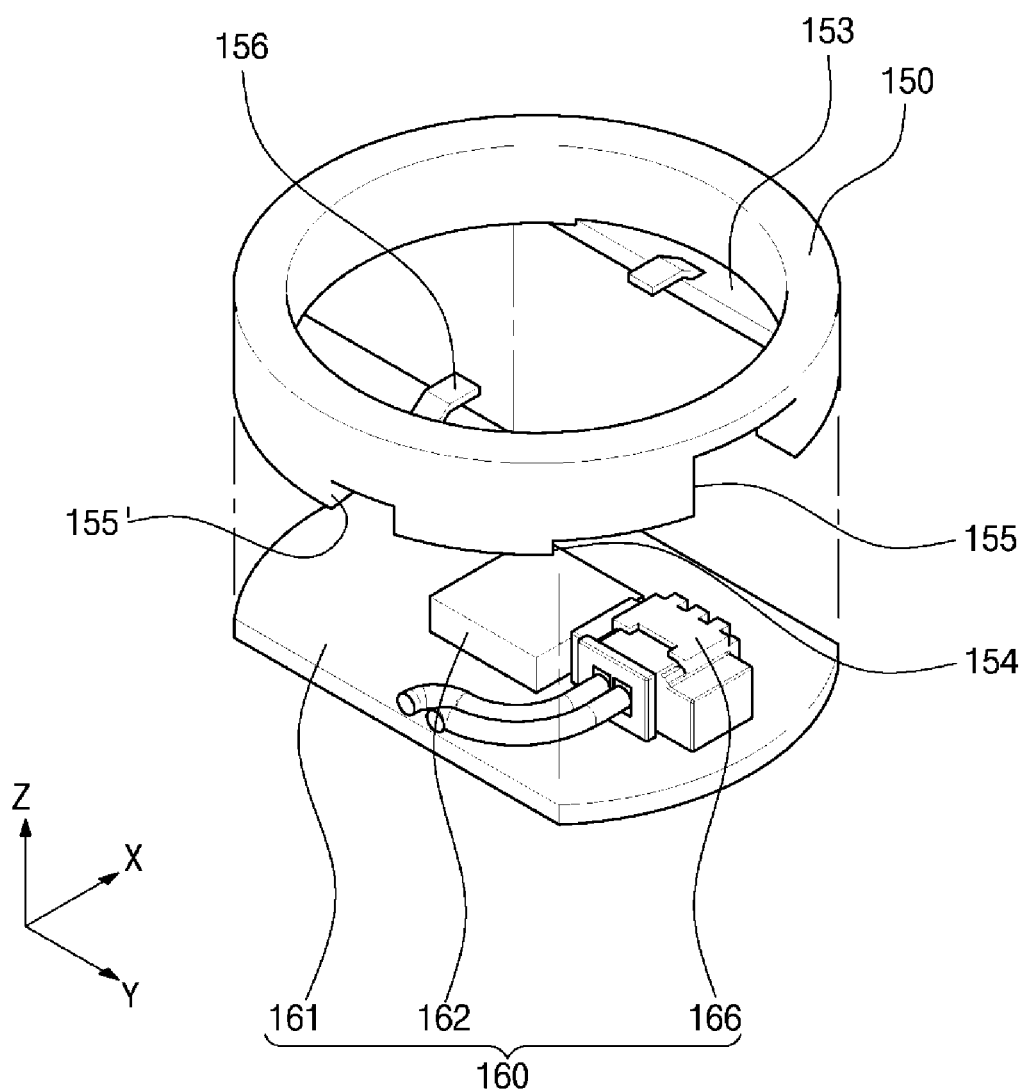
FIG. 17C is an exploded perspective view illustrating a coupling relationship between a sealing member and a light source unit according to an exemplary embodiment.

According to the illustrated exemplary embodiment as shown in FIGS. 17B and 17C, the board 161 may include metal. Accordingly, when the board 161 illustrated in FIGS. 1B and 1C is used, it may be difficult to form a pattern on the bottom surface of the board 161 provided with the light source 162. In this case, the pattern may refer to a pad, on which the light source 162, the connector 166, or the like may be provided.

Accordingly, according to the illustrate exemplary embodiment shown in FIGS. 17B and 17C, the light source 162 and the connector 166 are provided on the same side of the board 161.

Referring to FIG. 17B, the board 161 has a different shape from that of the through pipe 111. A light reflection layer may be provided on one surface of the board 161. The light reflection layer may be provided on the surface, on which the light source 162 is provided. In this manner, the light efficiency of the sterilization module may be improved by reflecting light emitted from the light source 162 and traveling towards the transparent member 140.

In some exemplary embodiments, a light reflection layer may also be provided on the inner side surface of the sealing member 150. As such, a portion of light emitted from the light source 162 and that does not travel straight along the z-axis direction may be reflected from the inner side surface of the sealing member 150, and then may be emitted toward a window.

The photocatalyst may be applied on the inner side surface of the sealing member 150 and the board 161. The photocatalyst is substantially the same as that described above. The photocatalyst may receive UV and generate a sterilization material, thereby preventing the contamination of the inner side surface of the sealing member 150 or the board 161.

The light reflection layer or the photocatalyst may include metal or metal oxide. Accordingly, the light reflection layer or the photocatalyst may be insulated from the light source 162, the connector 166, or the wiring part to prevent short circuit therebetween.

As will be described in more detail later, as the space between the board 161 and the sealing member 150 is sealed, it may be necessary to dissipate the heat generated from the light source 162 provided on the front surface of the board 161 to the rear surface of the board 161. As such, the board 161 may include a material of relatively high thermal conductivity.

For example, the board 161 may include metal. The metal may be an alloy of copper, aluminum, iron, or combinations thereof, without being limited thereto.

According to an exemplary embodiment, a waterproof resin is provided on the rear surface of the board 161, which will be described in more detail later.

The fastening member 170 may be further provided to fix the board 161. The fastening member 170 of FIG. 1 may be provided in the form of penetrating the board 161, however, the fastening member 170 according to the illustrated exemplary embodiment may be provided in the form of pressurizing the board 161 on one side.

For example, as illustrated in FIG. 17B, the fastening member 170 may be coupled in a screw manner to pressurize the board 161. However, the inventive concepts are not limited to the screw manner. In some exemplary embodiments, the fastening member 170 may be hooked to be fixed to the main body 110 and the sealing member 150 in a hooked manner.

When the fastening member 170 is provided in a screw manner, the screw thread provided on the outer surface of the fastening member 170 may be interlocked with the screw thread 113 of the main body 110. The fastening member 170 may be easily moved in the direction (z-axis direction) of the transparent member 140 by rotating the fastening member 170 along the screw thread 113 of the main body 110. In addition, as the fastening member 170 moves in the direction of the transparent member 140, components provided on the fastening member 170, such as the sealing member 150, the transparent member 140, the inner sealing member 121, and the main body 110, as well as the board 161, may be in a closer contact with the fastening member 170.

As the above-described components are more closely contacted by the fastening member 170, the watertight of the sterilization module according to an exemplary embodiment may be improved.

FIG. 17C is an exploded perspective view illustrating a coupling relationship between a sealing member and a light source unit according to an exemplary embodiment.

Referring to FIG. 17C, the coupling relationship between the sealing member 150 and the light source unit 160 is shown. The sealing member 150 may include the wing 153, which may be provided to the sealing member 150 in the form of a string formed in a circle.

The wing 153 may be provided as a plurality of pieces, and when two wings 153 are provided, the two wings 153 may be provided to the sealing member 150 to face each other. The size of the wing 153 is not particularly limited. However, the size and shape of the wing 153 may be determined, such that the sealing member 150 and the light source unit 160 are in close contact.

The wing 153 may be provided integrally with the sealing member 150 on the bottom surface of the sealing member 150. As such, a step 154 is provided on the bottom surface of the sealing member 150. The height of the step 154 is substantially the same as the thickness of the wing 153. In addition, the height of the step 154 may be substantially the same as the thickness of the board 161 of the light source unit 160. As such, the light source unit 160 may be inserted into a portion of the step 154 provided in the sealing member 150. Accordingly, when the sealing member 150 and the light source unit 160 are coupled, the bottom surface of the sealing member 150 and the bottom surface of the light source unit 160 may be continuously and flatly connected to each other. The width of the board 161 in the x-axis direction may be substantially the same as the distance between the two wings 153 of the sealing member 150. As such, when the light source unit 160 and the sealing member 150 are coupled, the sealing member 150 and the light source unit 160 may be sealed without a gap. In addition, when the sealing member 150 and the through pipe 111 are in close contact, because the size of the sealing member 150 is substantially the same as the size of the cross-section of the through pipe 111 of the main body, the space provided with the light source 162 may be completely sealed by coupling the light source unit 160 with the sealing member 150.

As such, even though the waterproof resin is filled on the rear surface of the board 161, the waterproof resin may not penetrate the front surface or the first surface the board 161 provided with the light source 162.

Concave parts 155 and 155' may be provided on the side surface of the sealing member 150. The locations of the concave parts 155 and 155' in the sealing member 150 may vary depending on the provision form of the light source unit 160. In particular, the concave parts 155 and 155' may be provided at the location where the connector 166 and the wiring part of the light source unit 160 are located. As such, even when the sealing member 150 and the board 161 are in close contact, the components of the light source unit 160 may not be damaged by the sealing member 150.

In addition, the concave parts 155 and 155' of the sealing member 150 may fix the wiring part and the connector 166. In particular, when the sealing member 150 and the board 161 are in close contact, the wiring part and the connector 166 provided in the concave parts 155 and 155' may be fixed without moving, even though the light source unit 100 is shaken or vibrated.

A fixing protrusion 156 may be provided to the wing 153. When the board 161 and the sealing member 150 are coupled, the fixing protrusion 156 prevents the board 161 from moving beyond the wing 153 in the z-axis direction of the wing 153. The number of the fixing protrusions 156 and the shapes thereof are not particularly limited. The fixing protrusion 156 may extend in the x-axis direction or the y-axis direction depending on the provision form of the wing 153. As such, the movement of the board 161 in the z-axis direction may be limited. At least one or more fixing protrusions 156 may be provided to the respective wing 153.

The board 161 corresponds to the shape of the open part defined by the sealing member 150 and the wing 153. Accordingly, when the sealing member 150 is circular and the wing 153 has the shape of the string provided in the circle, the board 161 may have the shape similar to a rectangle including two arcs and a straight line connecting two arcs. However, the shapes of the board 161, the wing 153, or the sealing member 150 are not limited thereto, and may be varied as needed.

However, even though the shapes of the board 161, the wing 153, or the sealing member 150 may be changed, the board 161 may have substantially the same shape as the open part defined by the sealing member 150 and the wing 153.

As described above, according to an exemplary embodiment, the sterilization module has a watertight structure. As such, it is possible to prevent moisture from penetrating into the sterilization module. In addition, even though the moisture penetrates into the sterilization module, the penetrated moisture may not infiltrate through the sterilization module into the device, in which the sterilization module is installed.

Figure 18A:
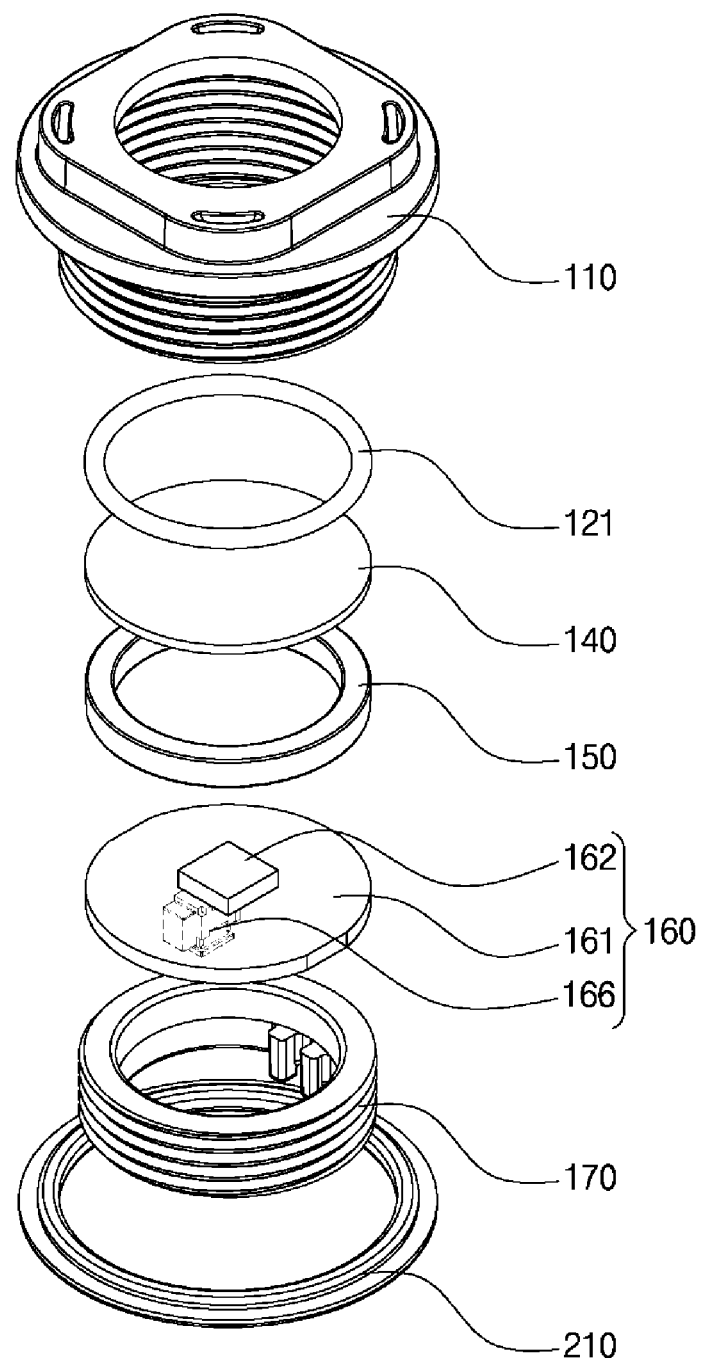
FIGS. 18A and 18B are exploded perspective views of a sterilization module according to another exemplary embodiment.
Figure 18B:
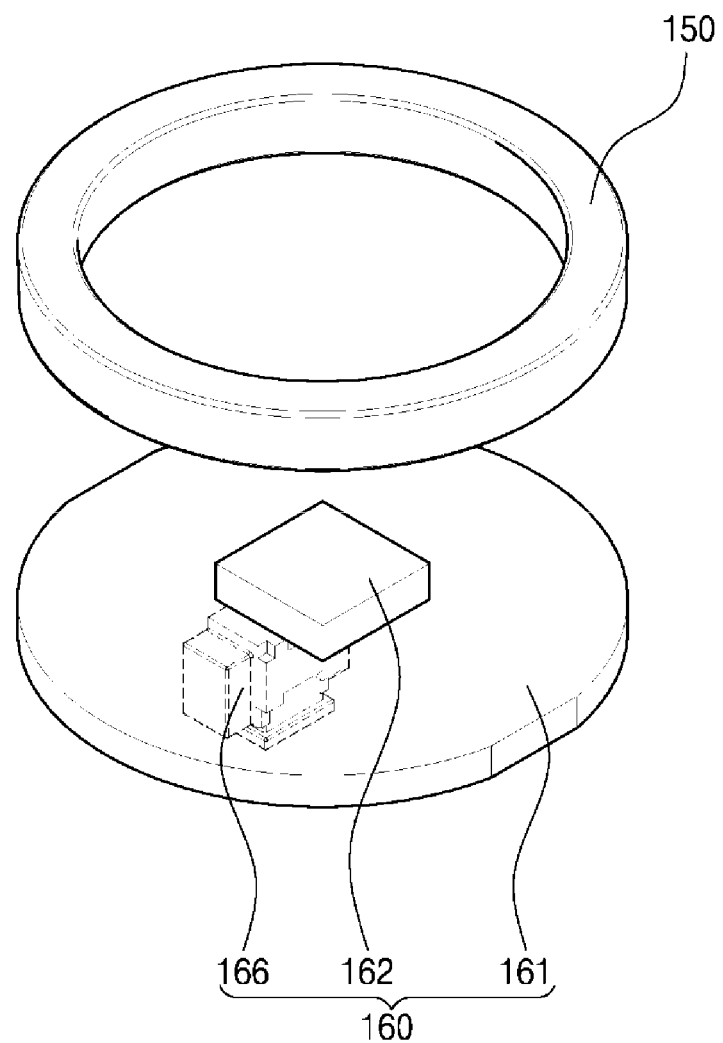

FIGS. 18A and 18B are exploded perspective views of a sterilization module according to another exemplary embodiment.

Hereinafter, repeated descriptions to the components of the sterilization module according to the illustrated exemplary embodiment that have the same configuration as the above-described will be omitted to avoid the redundancy.

Referring to FIG. 18A, the sterilization module includes the main body 110, the inner sealing member 121, and the light source unit 160. In addition, the light source unit 160 includes the circular board 161.

According to an exemplary embodiment, the shape of the board 161 corresponds to the shape of the cross-section of the through pipe 111 of the main body 110, and thus, the space between the main body 110 and the board 161 may be sealed without the sealing member 150. Accordingly, when waterproof resin is filled on the rear surface of the board 161, the waterproof resin may not penetrate beyond the board 161 or onto the front surface of the board 161.

FIG. 18A illustrates that the cross-section of the through pipe 111 and the board 161 are circular. However, the shapes of the cross section of the through pipe 111 and the board 161 are not limited thereto, and may have various other shapes, such as a square, a rectangle, a trapezoid, a rhombus, a triangle, an oval, a semicircle, and a semi-ellipse, and the like.

As the board 161 has a shape corresponding to the cross-section of the through pipe 111, the wing is not provided to the sealing member 150. Accordingly, the open part defined by the sealing member 150 also has a shape corresponding to the through pipe 111.

According to the illustrated exemplary embodiment shown in FIG. 18A, the board 161 includes a resin composition layer. For example, the board 161 may have a multi-layer structure including a resin composition layer. The resin composition layer included in the board 161 may be a glass fiber fabric or the like. The glass fiber fabric may be obtained by mixing the glass fiber, epoxy resin, phenolic resin, and the like.

In addition, the board 161 may include a metal layer provided on the resin composition layer. For example, the board 161 may have a form, in which a metal layer/a resin composition layer/a metal layer are stacked sequentially. In this case, the metal layer may include copper, silver, iron, aluminum, gold, or an alloy thereof.

When the board 161 including a resin composition layer is used, the light source 162 and the connector 166 may be provided to both surface of the board 161. As such, the light source 162 may be provided on one surface of the board 161, and the connector 166 may be provided on another surface of the board 161.

By providing the connector 166 and the light source 162 on different surfaces of the board 161, the size of the light source unit 100 as a whole may be reduced.

In addition, the light source 162 may be disposed closer to the transparent member 140 by providing the connector 166 and the light source 162 on different surfaces of the board 161. As such, the amount of light emitted from the light source 162 and blocked by the outer wall of the main body 110 may be reduced significantly. Also, there is less light blocked by the main body 110 by positioning the light source 162 to be close to the transparent member 140, thereby securing the relatively wider irradiation angle.

As described above, the wider irradiation angle may be secured by providing the connector 166 and the light source 162 on different surfaces of the board 161, and thus, it is also possible to reduce the size of the board 161. In this manner, the size of the sterilization module as a whole may also be reduced.

When the size of the sterilization module may be reduced, the size of the opening drilled in the outer wall, such as a reservoir or the like, may be reduced to install the sterilization module. As such, the leakage of water or the like penetrating into the opening may be prevented.

In addition, FIG. 18A illustrates that the upper portion of the main body 110 protrudes. However, according to FIG. 18A, the connector 166 is provided on the bottom surface of the board 161, and thus, the upper portion of the main body 110 may not need to protrude by the height of connector 166. Accordingly, in some exemplary embodiments, the upper portion of the main body 110 may be substantially flat without a protrusion part.

The sealing member 150 may fix the transparent member 140 by pushing the transparent member 140 in the z-axis direction. The sealing member 150 may also function as a spacer that separates the transparent member 140 from the board 161.

Referring to FIG. 18B, the coupling relationship between the sealing member 150 and the light source unit 160 is shown.

The sealing member 150 according to the illustrated exemplary embodiment does not include a step as that illustrated in FIG. 17C. This is because the shape of the board 161 is substantially the same as the shape of the cross-section of the through pipe 111.

When the sealing member 150 has a donut shape, the diameter of the sealing member 150 may be substantially the same as the diameter of the board 161. In addition, the inner diameter of the sealing member 150 may be less than the diameter of the board 161. As such, the sealing member 150 may function as a spacer, such that the board 161 does not contact the transparent member 140 provided on the sealing member 150.

While the light source 162 is protected, such that the light source 162 is not in contact with the transparent member 140, the height of the sealing member 150 may be a size capable of maximizing the irradiation angle of the light source 162. As the height of the sealing member 150 surrounding the light source 162 is higher, light emitted by the light source 162 in the lateral direction may be blocked by the sealing member 150. The height of the sealing member 150 may be a minimum height capable of protecting the light source 162, such that the light source 162 does not contact the transparent member 140.

Figure 19A:
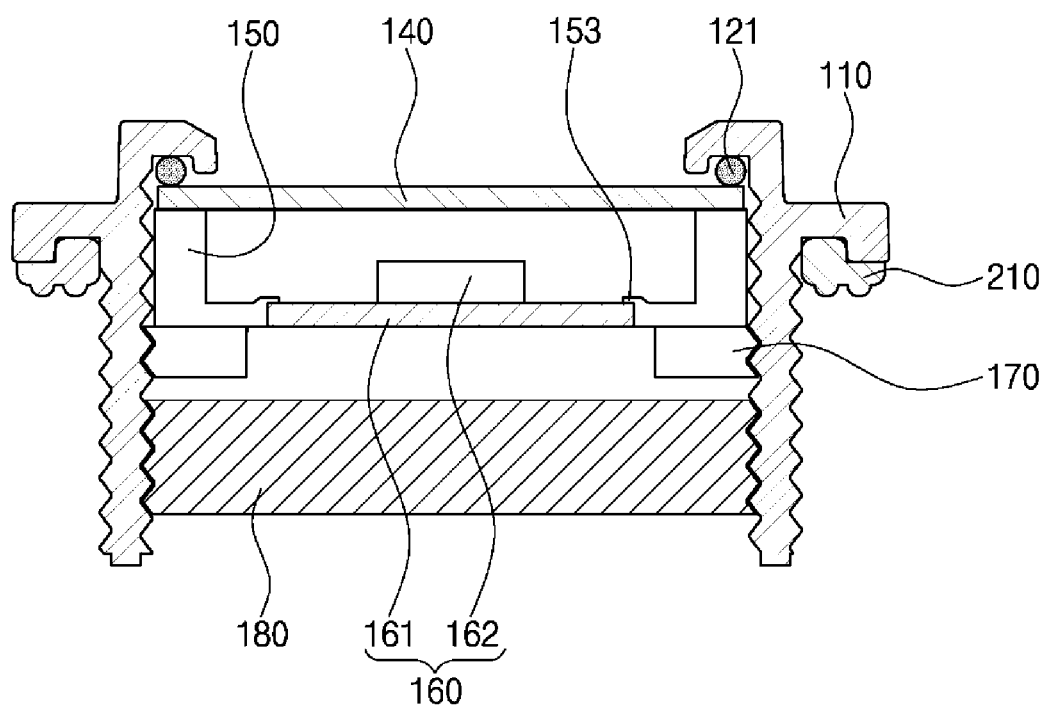
FIGS. 19A and 19B are cross-sectional views of a sterilization module according to another exemplary embodiment.
Figure 19B:
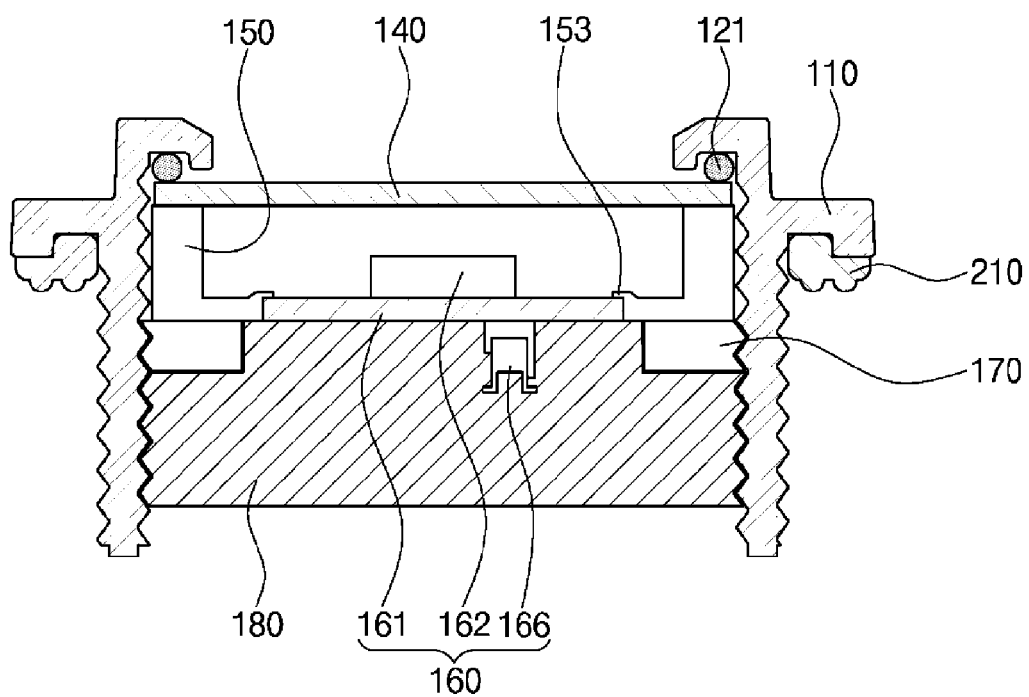

FIGS. 19A and 19B are cross-sectional views of a sterilization module according to another exemplary embodiment.

Referring to FIGS. 19A and 19B, a waterproof resin 180 is filled on the rear surface of the board 161 or on the second surface of the board 161. The waterproof resin 180 is made by hardening waterproof resin composition, and seals one side of the through pipe 111.

The waterproof resin composition may include at least one of epoxy resin, silicon oil, polyethylene, polypropylene, polyvinylchloride, polystyrene, acrylonitrile-butadiene-styrene (ABS) resin, methacrylate resin, polyamide, polycarbonate, polyacetyl, polyethylene terephthalate, modified polyphenylene oxide (MPO) resin, polybutylen terephthalate, polyurethane, phenolic resin, urea resin, melamine resin, and the combination thereof.

It is desirable that the waterproof resin 180 does not react with water and prevent the penetration of water.

In addition, it is desirable that the waterproof resin 180 is not deformed by heat. When the waterproof resin 180 is deformed by heat, the shape, the physical property, or the like of the waterproof resin 180 in the sterilization module may be changed when the reservoir, in which the sterilization module is installed is heated.

In particular, when a thermoplastic resin with low glass transition temperature is used, the waterproof resin 180 may be deformed due to the increase in ambient temperature or the heat released from the light source 162, and external moisture and water may penetrate into the sterilization module along the deformed gap. Accordingly, the waterproof resin 180 may be formed using the material with relatively high glass transition temperature.

In addition, the waterproof resin 180 may be manufactured using an easily molded waterproof resin composition, which may be relatively easy to apply the waterproof resin composition and harden the waterproof resin composition.

A thermal hardening method, a UV hardening method, a natural hardening method, or the like may be used to harden the waterproof resin composition. However, in some exemplary embodiments, for the purpose of improving the efficiency of the process, the natural hardening method may be used as a method of hardening the waterproof resin composition. The natural hardening method may refer to the hardening through drying after the waterproof resin composition is applied at room temperature. Accordingly, a separate heating process or a UV irradiation process may be obviated in the natural hardening method, thereby improving the efficiency of a process of manufacturing the sterilization module.

The waterproof resin composition may further include a hardener and/or a coupling agent to naturally harden the waterproof resin composition.

The process of filling the waterproof resin 180 may be performed in a low humidity environment. As such, the humidity of the inner space of the sterilization module sealed by the waterproof resin 180 and the transparent member 140 may be relatively low. When the internal humidity of the sterilization module is low, the condensation of water vapor inside the sterilization module may be prevented even though the internal temperature of the sterilization module is changed afterward.

As the waterproof resin 180 seals the inside of the sterilization module, the temperature of the board 161 provided inside the sterilization module is hardly affected by the external temperature. As such, even though the temperature of the environment where the sterilization module is installed increases or decreases, the temperature of the board 161 may be maintained constantly.

According to an exemplary embodiment, the temperature of the board 161 is maintained constantly, thereby ensuring the normal operation of the sterilization module even in an extreme environment at high or low temperatures.

The waterproof resin 180 may release heat generated inside the sterilization module to the outside. In this case, the thermal conductivity of the waterproof resin 180 is relatively high.

The carbon-based nanofiller, graphite nanoplatelets (GNPs), silica, carbon nanotubes, and the like may be mixed in the waterproof resin composition to increase the thermal conductivity of waterproof resin 180. For example, the waterproof resin composition may be a mixture of epoxy resin, a carbon-based nanofiller, and graphite nanopallets (GNPs).

According to an exemplary embodiment, a carbon-based nanofiller, GNPs, silica, carbon nanotube, and the like may be mixed with the mixture of diglycidyl ether of bisphenol-A (DGEBA), 2-ethyl-4-methylimidazole, and γ-aminopropyl-triethoxysilane to manufacture the waterproof resin composition.

The thermal conductivity of the waterproof resin 180 manufactured according to the illustrated exemplary embodiment is about 7.06 W/(m.K), and is significantly higher than the thermal conductivity of about 0.28 W/(m.K) of the general epoxy resin. Accordingly, even though the waterproof resin 180 seals the inside of the main body 110 provided with the light source unit 160, the heat generated from the light source unit 160 may be easily released to the outside of the main body 110. As such, the light source unit 160 may be prevented from failing due to the accumulation of heat generated from the light source unit 160 inside the main body 110.

Referring to FIG. 19A, the wings 153 provided on both sides of the sealing member 150 are in contact with the board 161. As such, when an unhardened waterproof resin composition is filled inside the main body 110, the waterproof resin composition may not penetrate toward the front surface of the board 161. As such, because the resin composition is in contact with the transparent member 140, light emitted from the light source 162 may not be obscured.

Referring to FIG. 19B, the shape of the board 161 corresponds to the shape of the cross-section of the through pipe 111. As such, the bottom of the sealing member 150 is in contact with the top surface of the board 161 without providing the wings 153 on the sealing member 150. Even in this case, there is no risk that the waterproof resin composition will penetrate toward the transparent member 140 beyond the board 161.

In particular, referring to FIG. 19B, the connector 166 is provided on the bottom surface of the board 161, and thus, the connector 166 is more likely to be exposed to the water penetrating into the rear surface of the light source unit 160. Accordingly, the waterproof resin 180 of FIG. 19B may be filled in a form of completely surrounding the connector 166.

Referring to FIGS. 19A and 19B, the outer sealing member 210 may be provided to the outside of the main body 110. When the sterilization module is installed in a reservoir, the outer sealing member 210 may seal a portion in which the sterilization module is installed, for example, the space between the reservoir inner wall and the sterilization module, such that the space is watertight. As such, the opening where the sterilization module is installed prevents water from leaking inside the reservoir.

The outer sealing member 210 may be formed of, but is not limited to, VITON®, ethylene propylene (E.P.R), TEFLON®, or KALREZ®.

The concave part capable of accommodating the outer sealing member 210 may be provided on the exterior appearance of the main body 110. As shown in FIGS. 19A and 19B, at least part of the outer sealing member 210 is inserted into the concave part provided in the exterior of the main body 110.

Figure 21:
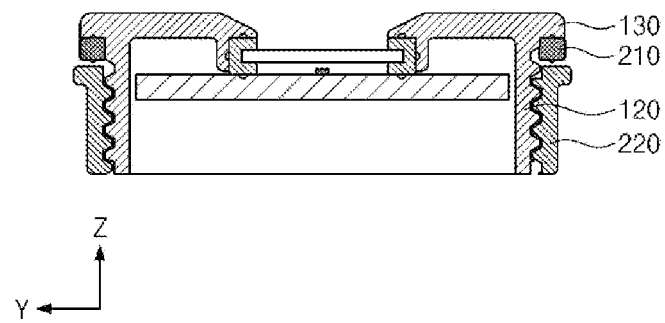
FIG. 21 is a cross-sectional view illustrating that an outer holder is coupled to a sterilization module.
Figure 22:
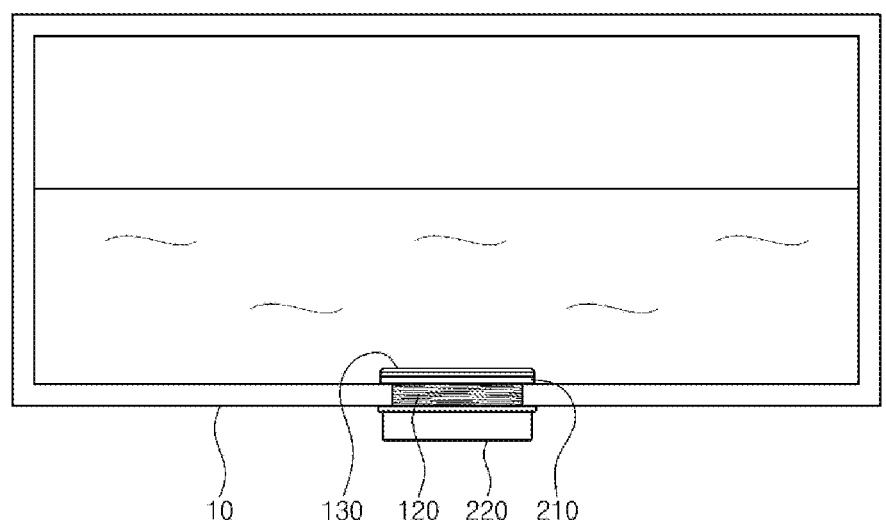
FIG. 22 is a cross-sectional view illustrating that a sterilization module is installed in an external device by using an outer holder.

FIGS. 20 to 22 are views for describing that the sterilization module of FIG. 1 is installed in an external device 10 by being coupled to the outer holder 220. In particular, FIG. 20 is an exploded perspective view illustrating that the outer holder 220 is coupled to the sterilization module of FIG. 1, FIG. 21 is a cross-sectional view illustrating that the outer holder 220 is coupled to the sterilization module, and FIG. 22 is a cross-sectional view illustrating that the sterilization module is installed in the external device 10 by using the outer holder 220.

Referring to FIGS. 20 and 21, the outer holder 220 is formed in a shape corresponding to the lower body 120. For example, as illustrated in FIGS. 20 and 21, the outer holder 220 is formed to have a cylindrical shape, in which the top and bottom surfaces are opened, and a screw thread is formed on the inner peripheral surface. The screw thread corresponding to the inner peripheral surface of the outer holder 220 is formed on the outer peripheral surface of the lower body 120. Accordingly, the outer holder 220 may be coupled to the lower body 120 by rotating along the screw thread of the lower body 120.

Furthermore, for the purpose of providing an additional waterproof structure between the main body 110 and the outer holder 220, the outer sealing member 210 may additionally be interposed between the main body 110 and the outer holder 220.

The outer sealing member 210 may have a shape corresponding to the upper body 130. For example, as illustrated in FIG. 20, the outer sealing member 210 may be formed in the shape of an O-ring. However, the inventive concepts are not limited thereto, as long as the waterproof structure may be provided between the main body 110 and the outer holder 220.

First to third protrusions for improving waterproof performance may be additionally formed on the top surface, the bottom surface, and the side surface of the outer sealing member 210, as in the sealing member 150 shown in FIG. 8.

Referring to FIG. 22, the sterilization module according to an exemplary embodiment is installed in the external device 10. The external device 10 may be, for example, a reservoir for storing water. The sterilization module may be installed in the reservoir to sterilize the water stored in the reservoir.

More closely referring to a method of installing the sterilization module, the upper body 130 of the sterilization module is inserted by penetrating from the inside of the external device 10 to the outside.

Afterward, the outer holder 220 is coupled to the outer wall of the lower body 120 outside the external device 10. For example, a screw thread is formed on the outer peripheral surface of the lower body 120, and the corresponding screw thread is formed on the inner peripheral surface of the outer holder 220. The outer holder 220 may be rotated along the screw thread of the lower body 120, and thus, the outer holder 220 may be coupled to the lower body 120.

In this case, while the outer holder 220 is coupled to the lower body 120, the outer holder 220 pressures the outer wall of the external device 10, and the bottom surface of the upper body 130 and the outer sealing member 210 pressurize the inner wall of the external device 10. Accordingly, the sterilization module is fixed to the external device 10. At this time, the outer sealing member 210 may be additionally interposed between the upper body 130 and the inner side surface of the external device 10, thereby preventing the water stored in the external device 10 from leaking outside the external device 10.

Referring to FIG. 22, when the sterilization module is installed on the bottom surface of the external device 10, a transparent member of a conventional sterilization module may be damaged by water pressure. However, as described above, the sterilization module according to an exemplary embodiment may be equipped with a transparent member 140 having a smaller size, as compared to that of the conventional sterilization module. Accordingly, the sterilization module according to an exemplary embodiment is less likely to be damaged by water pressure, and may be installed in the external device 10 that stores a large amount of water.

Meanwhile, in FIG. 21, the outer sealing member 210 is described as being interposed between the upper body 130 and the inner wall of the external device 10. However, the inventive concepts are not limited thereto. For example, in some exemplary embodiments, the outer sealing member 210 may be interposed between the lower body 120 and the outer wall of the external device 10.

Furthermore, in FIG. 22, the sterilization module is described as being installed on the bottom surface of the external device 10. However, the inventive concepts are not limited thereto. For example, in some exemplary embodiments, the sterilization module may be installed on the top surface or the side surface of the external device 10. When the sterilization module is installed on the top surface of the external device 10, the sterilization module may emit UV to the surface of the water stored in the external device 10. When the sterilization module is installed on the side surface of the external device 10, in other exemplary embodiments, the sterilization module may emit UV to the surface and/or the inside of the water stored in the external device 10.

As described with reference to FIGS. 1 to 22, the sterilization module according to exemplary embodiments includes the sealing member 150 for accommodating the transparent member 140 through a coupling groove formed therein. The sealing member 150 not only provides a waterproof function between the UV outlet 131 and the transparent member 140, but also function as a spacer to prevent pressure damage of the light source 162 between the board 161 and the transparent member 140.

As such, the sterilization module according to the exemplary embodiments is advantageous in miniaturization and cost reduction, by providing the waterproof function and the spacer function by using the sealing member 150 without providing a separate spacer. In addition, as the distance between the transparent member 140 and the light source 162 decreases, the path by which the force that pressures the board 161 reaches the transparent member 140 may be shortened. Accordingly, the waterproof efficiency may be increased.

Moreover, for the purpose of protecting the light source 162, the sterilization module according to exemplary embodiments may not include a separate quartz-type protective tube formed to surround the light source 162. More particularly, the sterilization module according to exemplary embodiments only the transparent member 140 installed in the UV outlet 131. In this manner, the transparent member 140 not only blocks the sterilization module from the outside, but also protects the light source 162. Accordingly, the sterilization module according to exemplary embodiments is more advantageous for miniaturization.

Meanwhile, the sterilization module according to exemplary embodiments may be provided to a user in the form of the completely assembled package, such that the user may easily install the sterilization module to the external device 10 by coupling the assembled sterilization module with the outer holder 220. However, in some exemplary embodiments, the sterilization module may be provided to the user without being assembled.

The sterilization module illustrated above is being described as including the outer holder 220 and the outer sealing member 210 for being coupled with the external device 10. Hereinafter, various modified forms of the outer holder 220 and the outer sealing member 210 will be described in more detail.

Figure 23A:
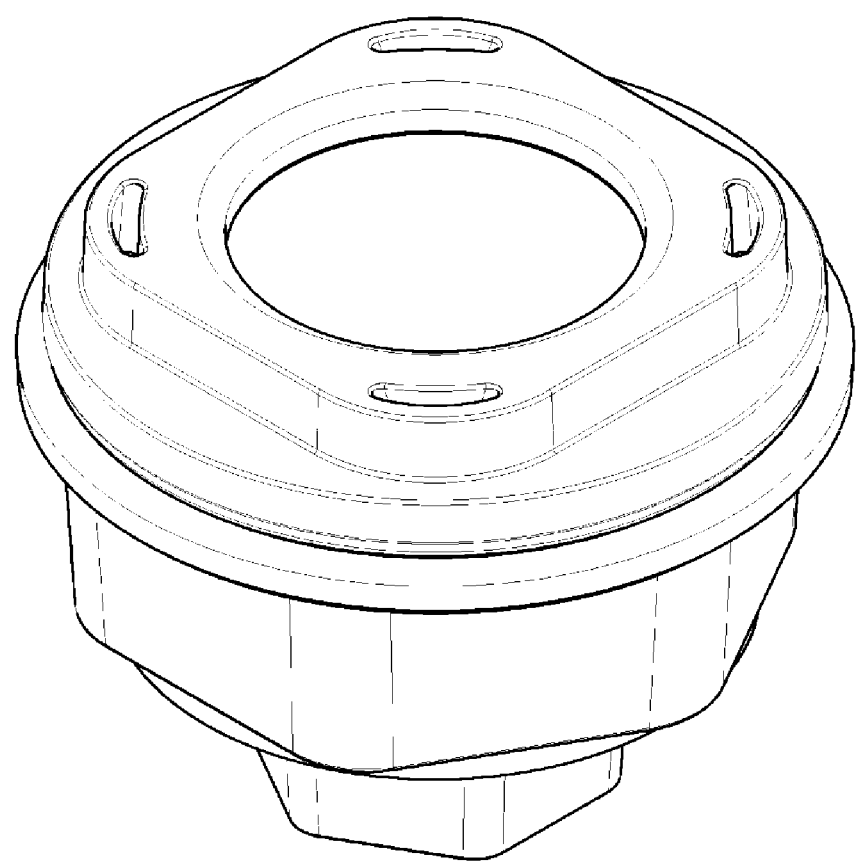
FIG. 23A is a perspective view of a sterilization module according to an exemplary embodiment.
Figure 23B:
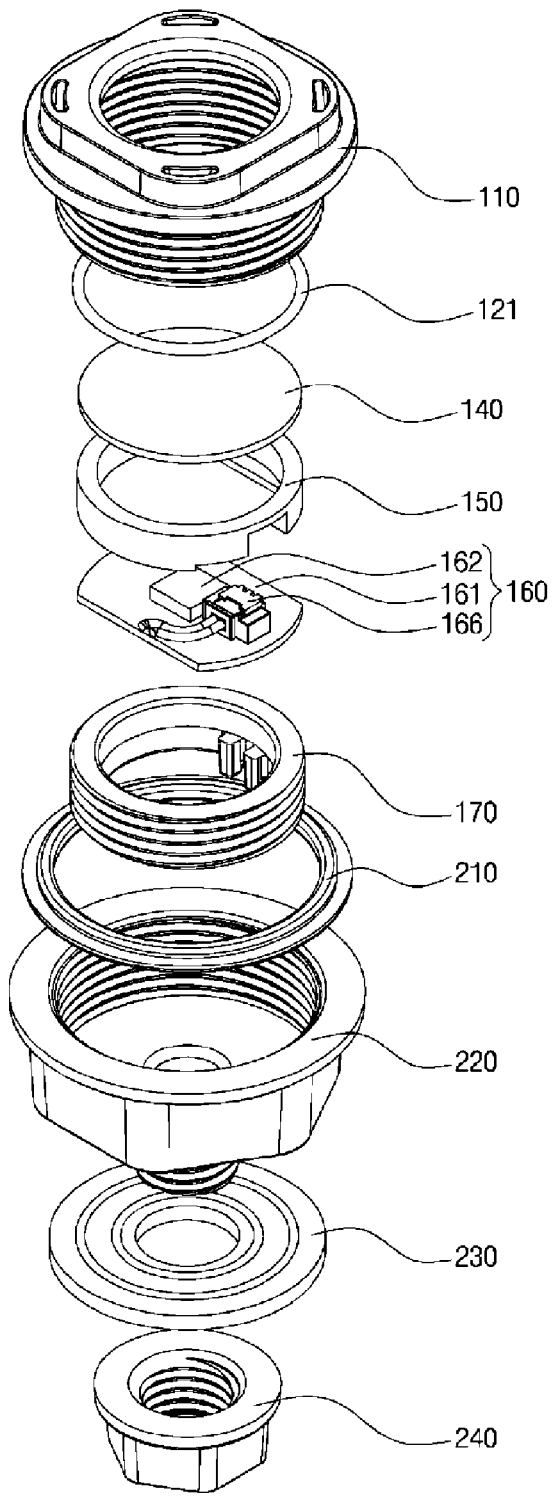
FIG. 23B is an exploded perspective view of a sterilization module according to an exemplary embodiment.
Figure 23C:
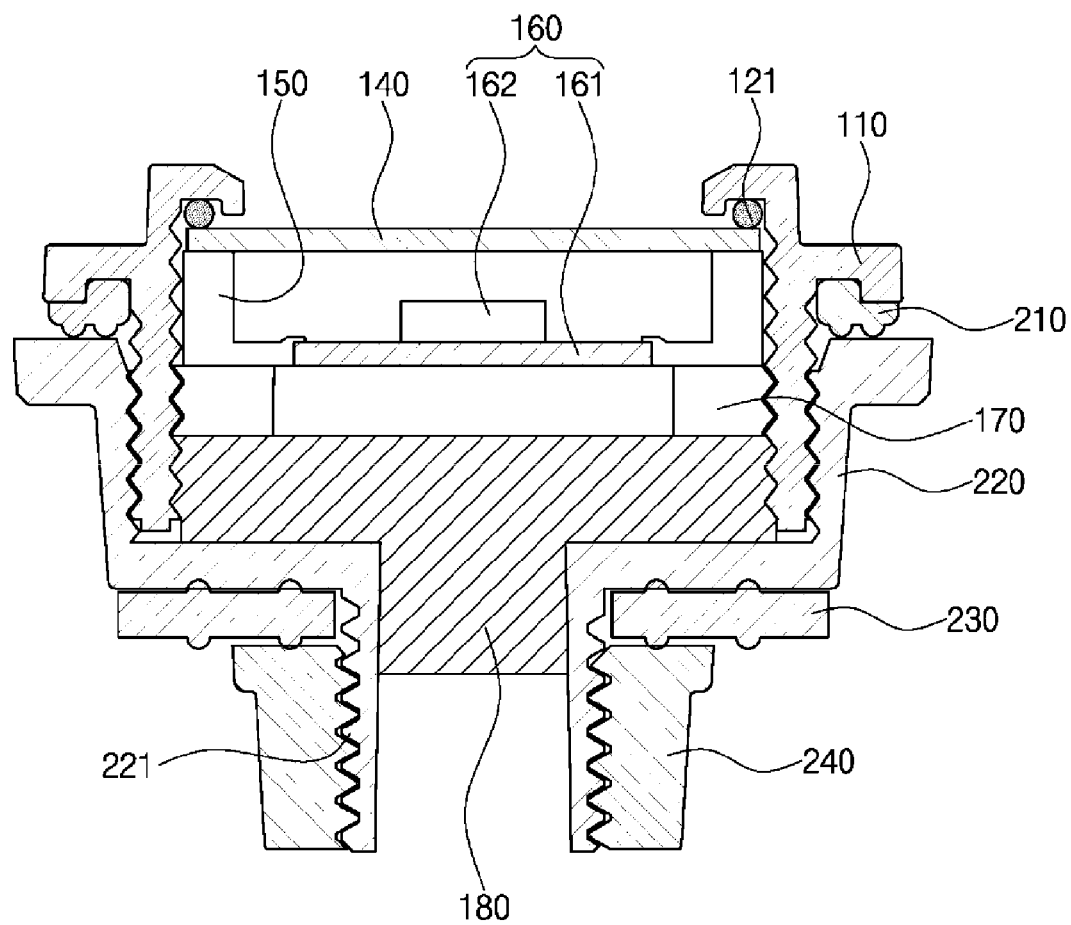
FIG. 23C is a cross-sectional view of a sterilization module according to an exemplary embodiment.

FIG. 23A is a perspective view of a sterilization module according to an exemplary embodiment. FIG. 23B is an exploded perspective view of a sterilization module according to an exemplary embodiment. FIG. 23C is a cross-sectional view of a sterilization module according to an exemplary embodiment.

Figure 23D:
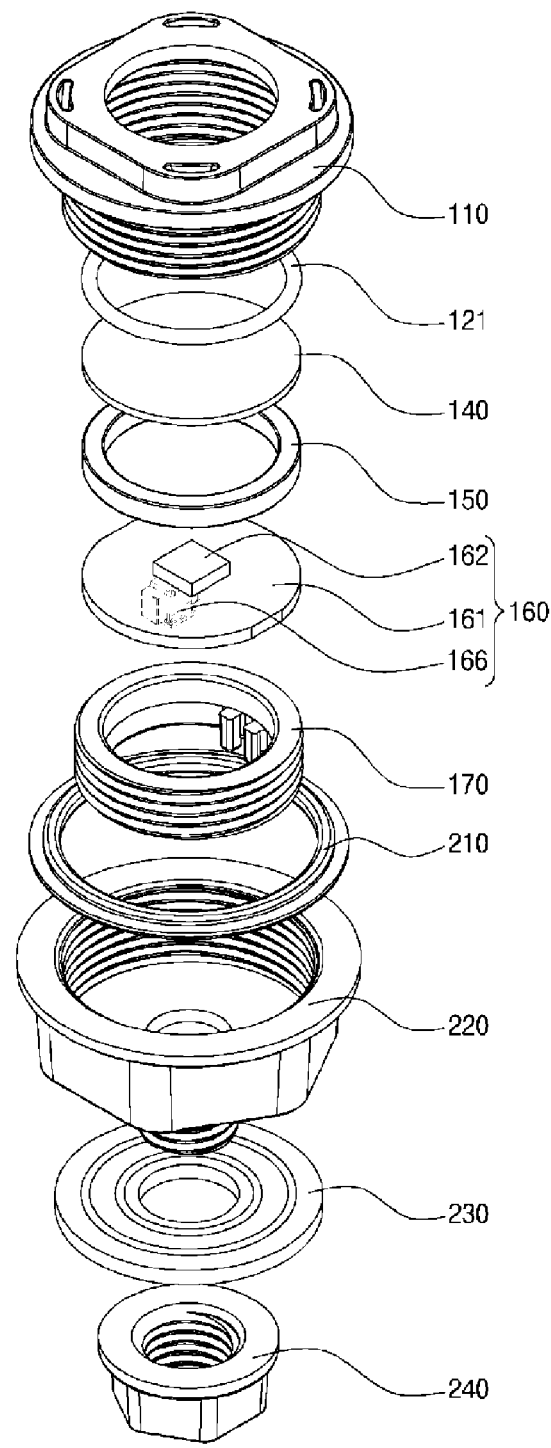
FIG. 23D is an exploded perspective view of a sterilization module according to another exemplary embodiment.
Figure 23E:
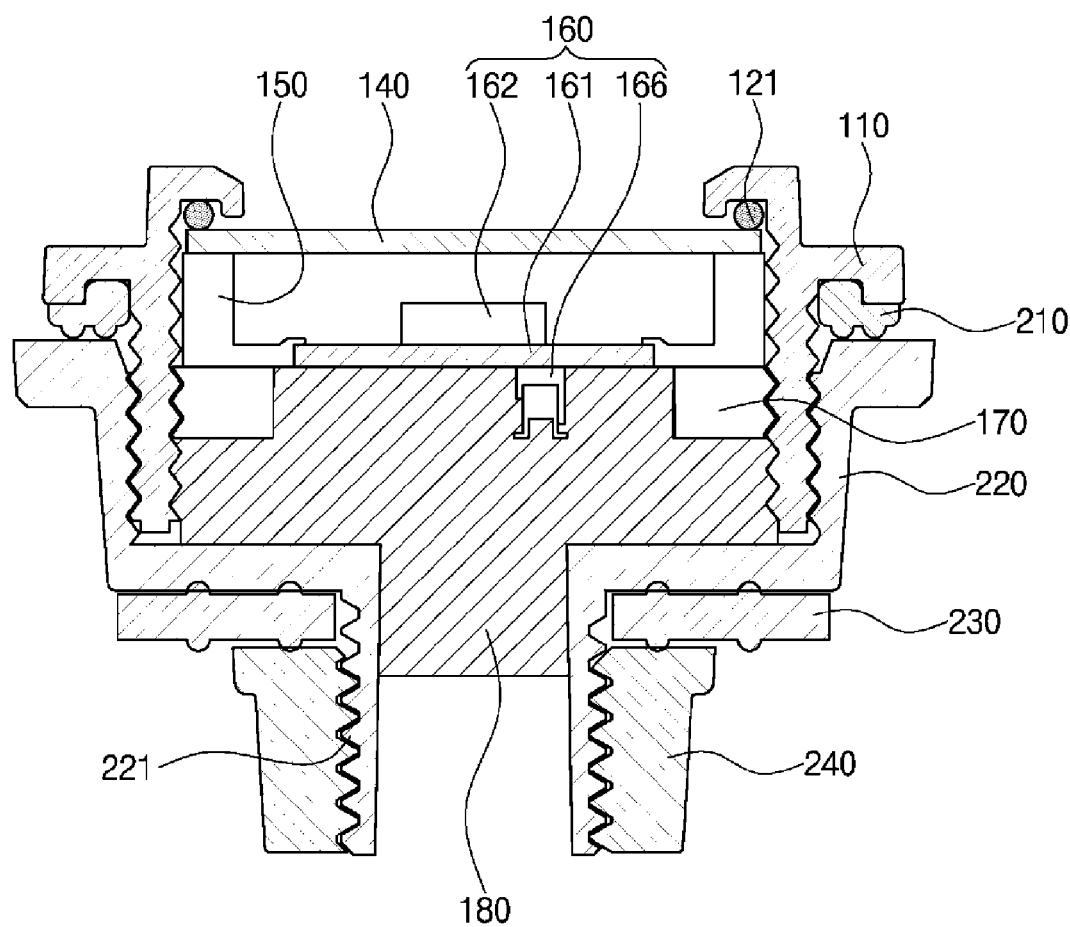
FIG. 23E is a cross-sectional view of a sterilization module according to another exemplary embodiment.

In addition, FIGS. 23D and 23E are an exploded perspective view and a cross-sectional view of a sterilization module according to another exemplary embodiment.

Hereinafter, a sterilization module according to an exemplary embodiment will be described with reference to FIGS. 23A to 23E.

The sterilization module according to the illustrated exemplary embodiment may further include the outer holder 220. As described above, the outer holder 220 may be coupled to the main body 110.

As illustrated in FIGS. 23B and 23C, when the main body 110 has a screw thread, the outer holder 220 may have a screw thread corresponding to the screw thread of the main body 110. As such, the main body 110 and the outer holder 220 may be coupled in a screw manner.

However, the coupling scheme between the outer holder 220 and the main body 110 is not limited to a screw type. In some exemplary embodiments, for example, the outer holder 220 and the main body 110 may be detachably coupled using a hook.

When the main body 110 and the outer holder 220 are coupled in the screw manner, a waterproof tape may be further provided between the screw thread of the main body 110 and the screw thread of the outer holder 220. The waterproof tape may be Teflon® (PTFE), polyethyl terephthalate (PET), acrylic resin, urethane resin, polyvinyl chloride (PVC), or the like. The waterproof tape may be relatively thin and elastic, and thus, may be in close contact with the screw thread. As such, when the screw thread of the main body 110 is coupled to the corresponding screw thread of the outer holder 220, the waterproof tape may fill the space between the two screw threads, and thus, water may be prevented from penetrating between the screw threads.

The shape of the main body 110 and the shape of the outer holder 220 may not need to be identical. In particular, when the coupling part of the main body 110 is circular, an outer holder coupling part 221 may be circular or have another shape. For example, as illustrated in drawings, when the coupling part of the main body 110 is circular, the outer holder coupling part 221 may be square. As such, even when the coupling part of the main body 110 does not have a shape mating the shape of the coupling part of the reservoir to be assembled, the sterilization module may be installed by including the outer holder 220 having the outer holder coupling part 221 corresponding to the shape of the coupling part of the reservoir to be assembled.

In addition, the shape of the exterior of the main body 110 may also be different from the shape of the exterior of the outer holder 220. For example, the exterior of the main body 110 may have a circular shape, and the exterior of the outer holder 220 may have a polygonal shape. When the sterilization module is installed in the reservoir in the screw manner, the user may easily grip the outer holder 220 having a polygonal shape.

Furthermore, when the coupling part of the main body 110 is compared with the coupling part of the outer holder 220, the size of the coupling part of the outer holder 220 may be less than the size of the coupling part of the main body 110. The size of the coupling part will be described in more detail later with reference to FIGS. 24A and 24B.

An auxiliary sealing member 230 and an outer auxiliary holder 240 may be provided to the outer holder coupling part 221.

When a sterilization module including the outer holder 220 is installed in a reservoir or the like, the auxiliary sealing member 230 may prevent water from leaking along the opening formed in the reservoir to install the sterilization module.

The auxiliary sealing member 230 may be made of an elastic material, and the low reactivity with water. The auxiliary sealing member 230 may be formed of, but is not limited to, VITON®, ethylene propylene (E.P.R), TEFLON®, or KALREZ®.

The outer auxiliary holder 240 is a member for fixing the sterilization module including the outer holder 220 to the reservoir or the like. Accordingly, the outer auxiliary holder 240 and the sterilization module are provided to be spaced from each other with the inner wall of the reservoir or the like interposed therebetween. The outer auxiliary holder 240 may have a screw thread corresponding to the outer holder coupling part 221 of the outer holder 220. As such, the sterilization module may be fixed to the inner wall of the reservoir or the like by rotating and coupling the outer auxiliary holder 240.

In addition, the auxiliary sealing member 230 may be provided on the same surface as the surface provided with the outer auxiliary holder 240, or may be provided on the same surface as the surface provided with the sterilization module. In particular, the auxiliary sealing member 230 may be provided inside or outside the reservoir. The installation location of the auxiliary sealing member 230 is not particularly limited, and may be determined in consideration of the whole size of the sterilization module.

The waterproof resin 180 fills the main body 110 and at least a part of the inside of the outer holder coupling part 221 of the outer holder 220. The inside of the outer holder coupling part 221 has a hollow structure, such as the through pipe 111 of the main body 110, and thus, the waterproof resin 180 may be filled inside the outer holder coupling part 221.

At this time, the amount of the waterproof resin 180 to be filled may vary as needed. Accordingly, the waterproof resin may also be filled in the inside of the main body 110 and the outer holder coupling part 221 of the outer holder 220, such that the waterproof resin 180 is in contact with the bottom surface of the board 161. However, in some exemplary embodiments, the waterproof resin 180 may be filled to fill only the part of the outer holder coupling part 221. However, for the purpose of improving the waterproof function, it is desirable to fill the waterproof resin 180 to seal one side of the outer holder coupling part 221.

The outer holder 220 shown in FIGS. 23A and 23B may be applied to the sterilizing module including the sealing member 150 that includes a wing or that does not include a wing.

Referring to FIGS. 23D and 23E, the light source 162 and the connector 166 are provided on different surfaces of the board 161. As can be seen in FIG. 23E, in this case, the waterproof resin 180 may be provided to completely surround the connector 166.

FIGS. 24A to 24D are cross-sectional views illustrating that a sterilization module is installed according to an exemplary embodiment.

Figure 24A:
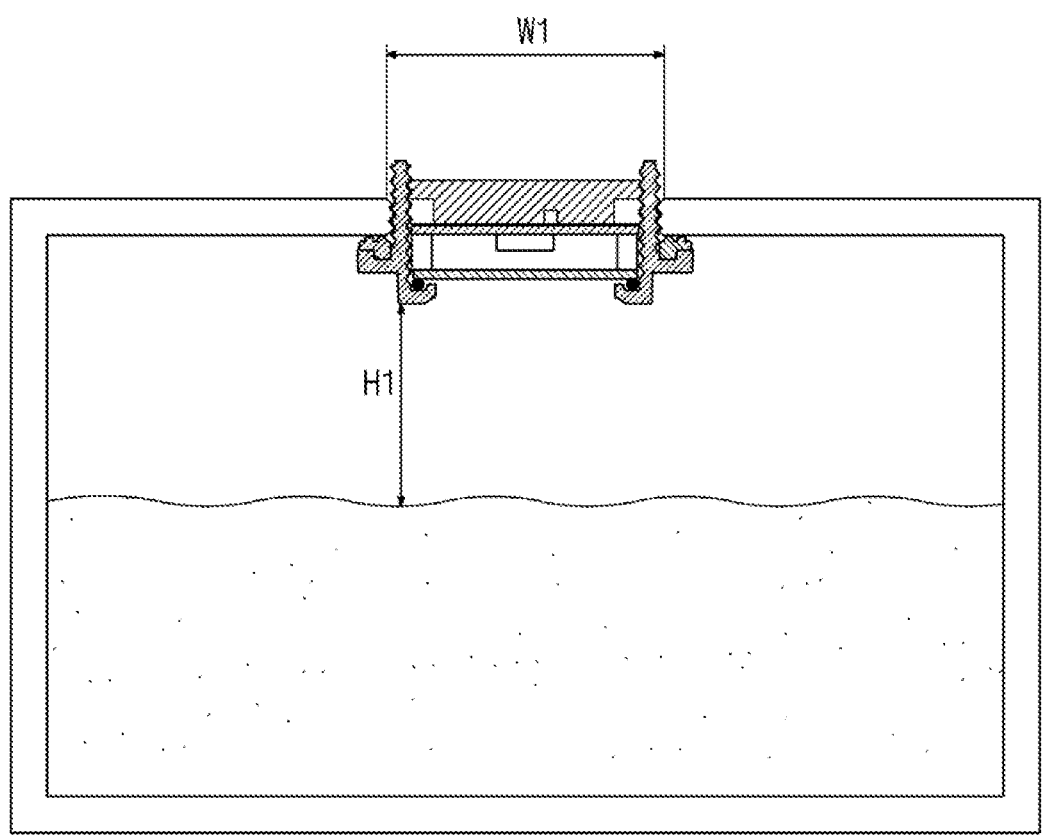
FIGS. 24A, 24B, 24C, and 24D are cross-sectional views illustrating that a sterilization module according to an exemplary embodiment is installed.
Figure 24B:
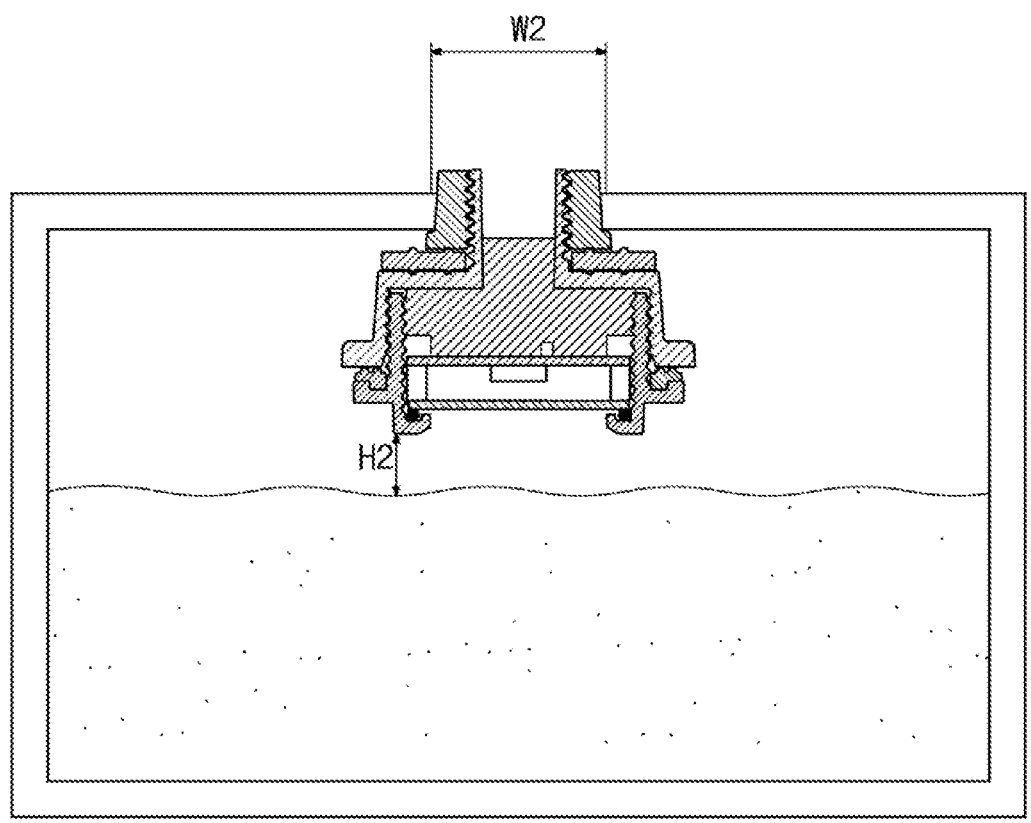
Figure 24C:
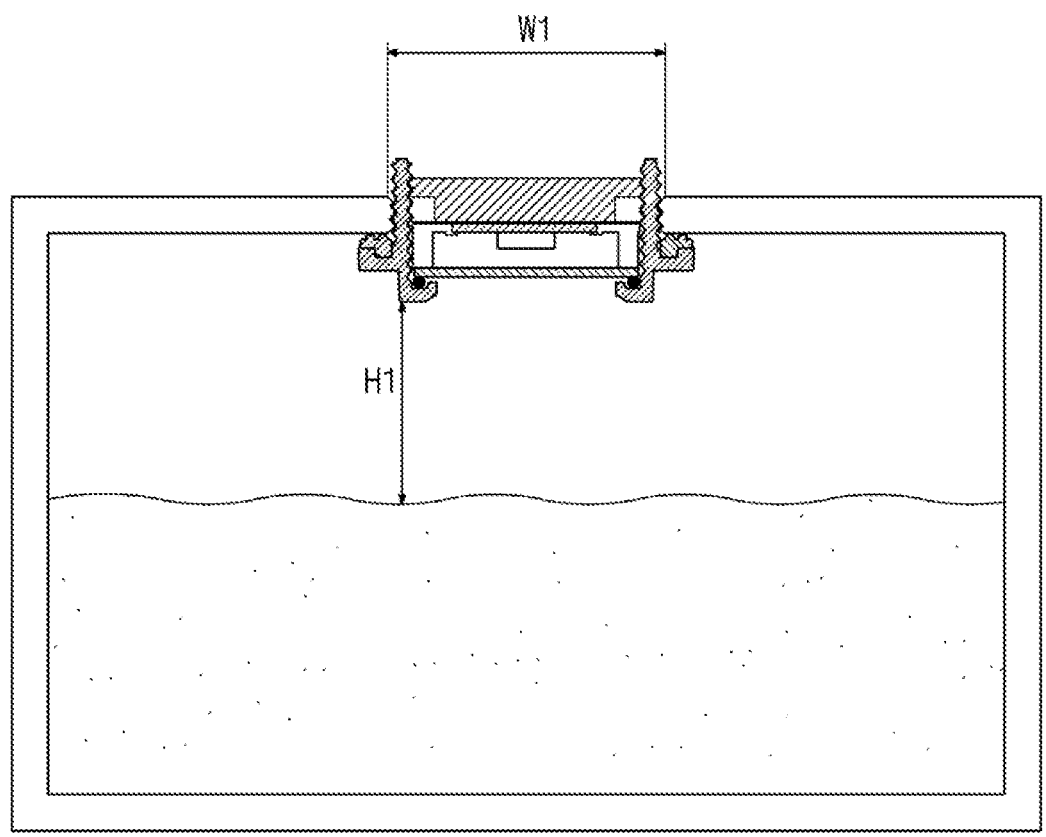
Figure 24D:
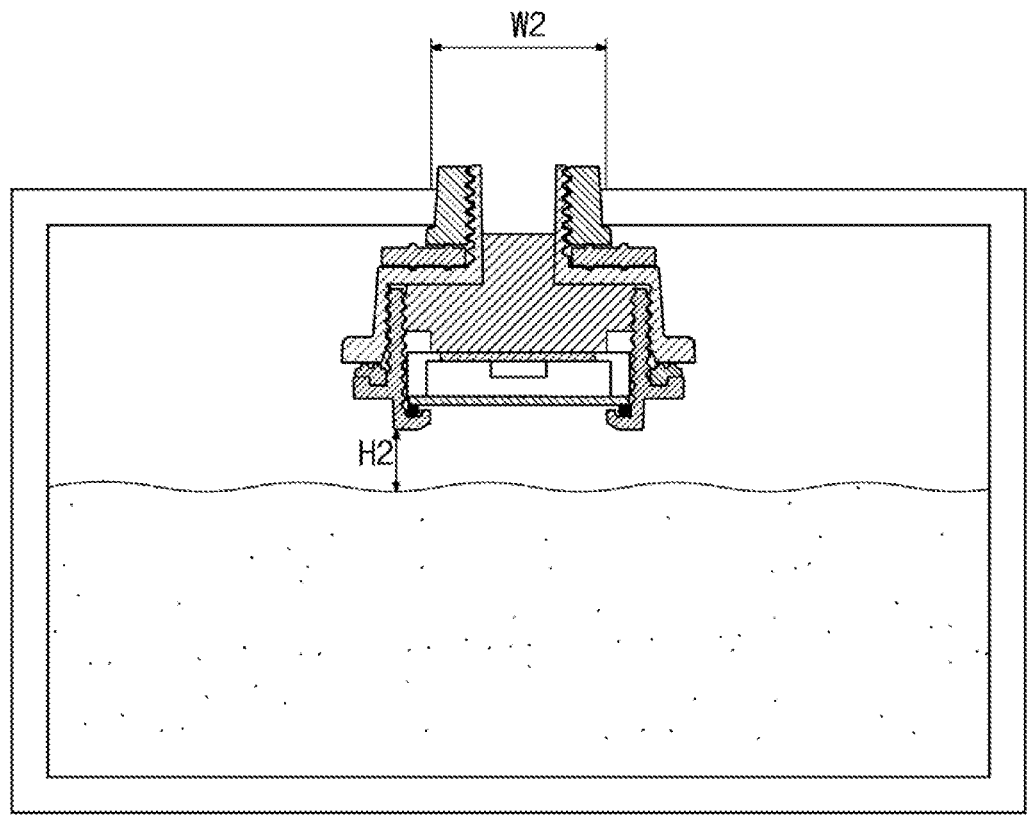

Referring to FIGS. 24A and 24C, a sterilization module without an auxiliary body is installed in a reservoir. On the other hand, referring to FIGS. 24B and 24D, a sterilization module including an auxiliary body is installed in the reservoir. Hereinafter, the form in which the sterilization module is installed will be described with reference to FIGS. 24A to 24D.

The sterilization module is coupled to the opening provided in the outer wall of the reservoir. The opening provided in the outer wall of the reservoir may have a screw thread corresponding to the screw thread provided in the main body or the auxiliary body of the sterilization module.

According to the exemplary embodiments shown in FIGS. 24A and 24C, the opening provided in the outer wall of the reservoir has a first width W1. On the other hand, according to the exemplary embodiments shown in FIGS. 24B and 24D, the opening provided in the outer wall of the reservoir has a second width W2. The first width W1 is relatively greater than the second width W2.

The second width W2 is less than the first width $W_1$. It may be sufficient to have a relatively small opening when a sterilization module employing an auxiliary body is installed. As such, the leakage of water in the reservoir through the opening may be relatively reduced.

In addition, as the size of the opening is small, the stress applied to the reservoir is relatively low, due to the opening and the sterilization module coupled to the opening.

The height between the sterilization module and the water surface varies depending on whether an auxiliary module is present. The height H2 (when the auxiliary module is included) is smaller than the height H1 (when the auxiliary module is not included). Accordingly, when including the auxiliary module, the sterilization module may be provided closer to the surface of water.

As such, the amount of light irradiated to water stored in the reservoir may be increased. In particular, when the sterilization module is provided close to the surface of water, light emitted from the sterilization module may be irradiated to water regardless of the emission angle. Accordingly, the sterilization efficiency to water may be improved when the sterilization module includes the auxiliary module.

Figure 25:
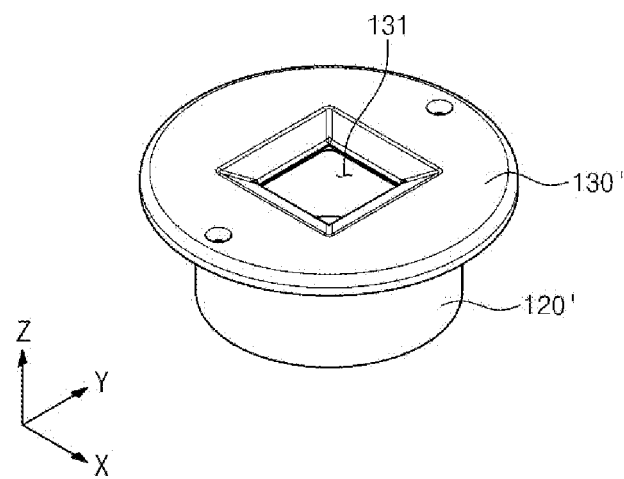
FIG. 25 is a perspective view of a main body according to an exemplary embodiment.
Figure 26:
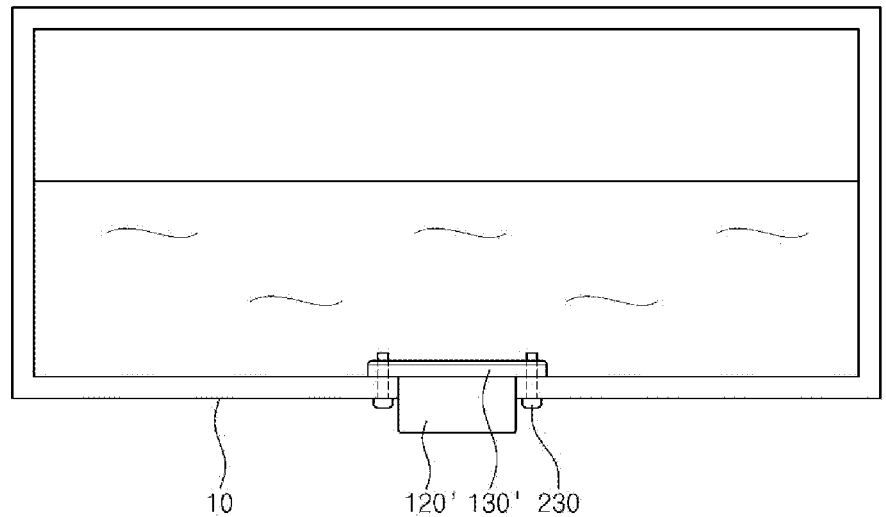
FIG. 26 is a cross-view illustrating that a sterilization module having a main body of FIG. 25 is installed in an external device.

FIGS. 25 and 26 are views illustrating a main body 110' according to an exemplary embodiment. In particular, FIG. 25 is a perspective view of the main body 110' according to an exemplary embodiment, and FIG. 26 is a view illustrating that a sterilization module 100' having the main body 110' of FIG. 25 is installed in the external device 10.

The sterilization module 100' of FIGS. 25 and 26 is similar to the sterilization module described in FIGS. 1 to 24. Accordingly, the same or similar components will be indicated with the same or similar reference numeral, and repeated descriptions thereof will be omitted to avoid redundancy.

Referring to FIGS. 25 and 26, the sterilization module 100' according to an exemplary embodiment includes the main body 110', and the main body 110' includes a lower body 120' and an upper body 130'.

Unlike the main body 110 of the sterilization module of FIG. 1, the main body 110' of the sterilization module 100' of FIG. 25 does not require the outer holder 220 for being coupling to the external device 10.

In particular, the screw thread for being coupled to the outer holder 220 is not formed in the outer peripheral surface of the lower body 120' of the main body 110' of FIG. 25. Instead, a coupling hole 139 for accommodating the external fastening member 230 is formed in the upper body 130' of the main body 110' of FIG. 25. For example, the external fastening member 230 may be a screw, and a screw groove may be formed on the inner peripheral surface of the upper body 130'.

In this case, as illustrated in FIG. 26, the upper body 130' of the sterilization module 100' is inserted by penetrating from the inside of the external device 10 to the outside. Afterward, the external fastening member 230 is coupled to the coupling hole 139 of the upper body 130' in the screw coupling method, and thus, the sterilization module 100' may be installed in the external device 10.

At this time, the sealing member, such as an O-ring, may be additionally interposed between the upper body 130 and the inner wall of the external device 10, thereby preventing water stored in the external device 10 from leaking outside the external device 10.

Figure 27:
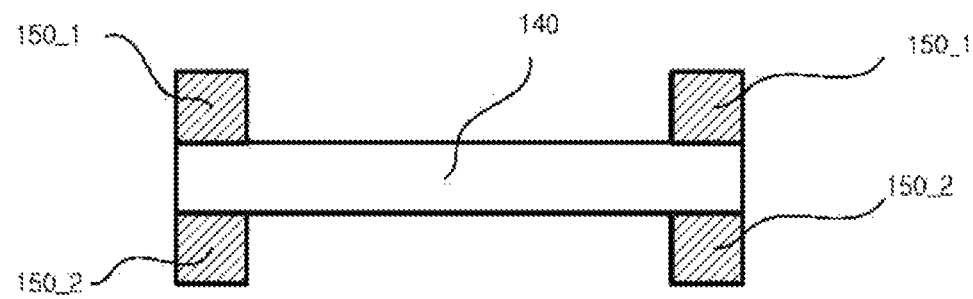
FIG. 27 is a cross-sectional view illustrating first and second sealing members according to an exemplary embodiment.
Figure 28:
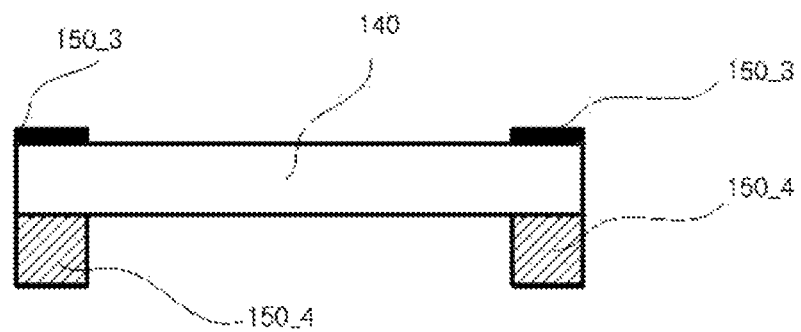
FIG. 28 is a cross-sectional view illustrating an adhesive member and a sealing member according to an exemplary embodiment.

FIGS. 27 and 28 are views illustrating sealing members according to exemplary embodiments. In particular, FIG. 27 is a cross-sectional view illustrating first and second sealing members 150_1 and 150_2 according to an exemplary embodiment, and FIG. 28 is a cross-sectional view illustrating an adhesive member 150_3 and a sealing member 150_4 according to another exemplary embodiment.

The sterilization module 100' of FIGS. 27 and 28 is similar to the sterilization module described in FIGS. 1 to 24. Accordingly, the same or similar components will be indicated with the same or similar reference numeral, and repeated descriptions thereof will be omitted.

Referring to FIG. 27, the sealing member may be divided into a first sealing member 150_1 and a second sealing member 150_2. In particular, the sealing member may be mounted to the transparent member 140, using the independent first sealing member 150_1 and the independent second sealing member 150_2.

The first sealing member 150_1 is interposed between the seating part 134 (refer to FIGS. 4 and 5) and the transparent member 140, and functions as a waterproof member that prevents water from penetrating through the UV outlet 131. The second sealing member 150_2 is interposed between the board 161 (refer to FIG. 1) and the transparent member 140, and functions as a spacer that allows a predetermined spaced distance to be formed between the board 161 and the transparent member 140.

The protrusions as illustrated in FIG. 8 may be formed on the top and bottom surfaces of the first and second sealing members 150_1 and 150_2. In this case, waterproof performance may be further improved.

Referring to FIG. 28, unlike FIG. 27, the adhesive member 150_3 may be interposed between the transparent member 140 and the seating part 134, instead of the first sealing member 150_1. In this case, the adhesive member 150_3 may allow the transparent member 140 to be firmly fixed without falling off from the seating part 134.

The adhesive member 150_3 may be formed using a material having adhesive force. Furthermore, the adhesive member 150_3 may be formed using a material having a waterproof function. For example, the adhesive member 150_3 may be a double-sided tape having waterproof performance. The seating part 134 and the transparent member 140 are firmly bonded by the double-sided tape-type adhesive member 150_3, thereby improving the waterproof performance of the sterilization module.

Figure 29:
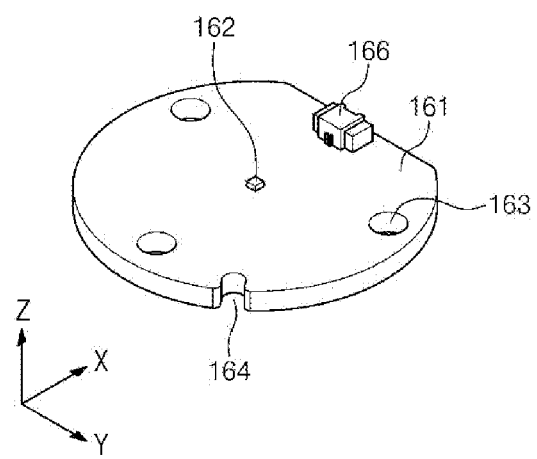
FIG. 29 is a perspective view of a light source unit according to an exemplary embodiment.

FIG. 29 is a view illustrating a light source unit 160' according to an exemplary embodiment. In particular, FIG. 29 is a perspective view of the light source unit 160' according to an exemplary embodiment.

The sterilization module and the light source unit 160' of FIG. 29 are similar to the sterilization module and the light source unit 160 described above. Accordingly, the same or similar components will be indicated with the same or similar reference numeral, and repeated descriptions thereof will be omitted.

Referring to FIG. 29, the light source unit 160' according to an exemplary embodiment includes the board 161, the light source 162, the light source unit coupling part 163, the support groove 164, the connecting passage 165, and the connector 166.

Unlike the light source unit 160 illustrated in FIG. 9, the light source unit 160' of FIG. 29 additionally includes a connector 166. As shown, the connector 166 may be mounted on the top surface of the board 161 and electrically connected to the board 161. Furthermore, the connector 166 may deliver the power supplied from the outside to the light source 162, and may be electrically connected to an external power device or a cable.

Figure 30:
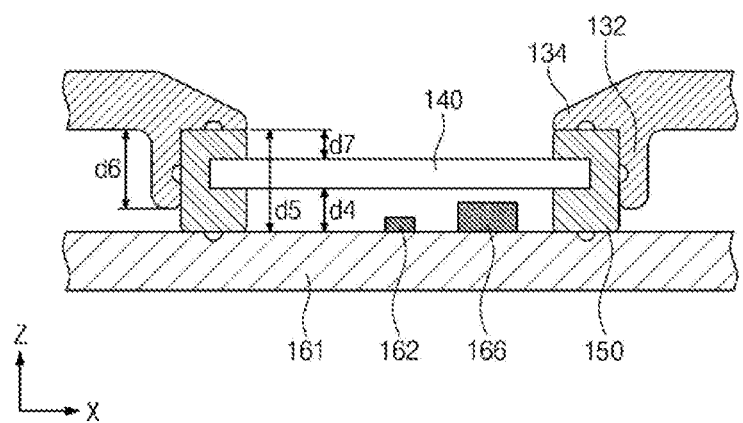
FIG. 30 is a cross-sectional view illustrating a light source unit.

Referring to FIG. 30, when the connector 166 and the board 161 are mounted on the upper surface of the connector 166, the transparent member 140 and the board 161 need to be spaced apart from each other at a predetermined width d4, to prevent the connector 166 from being damaged. Since the size of the connector 166 is greater than that of the light source 162, which is an LED chip, the separation distance d4 of FIG. 29 for protecting the connector 166 may be greater than the separation distance d1 of FIG. 16 for protecting the light source 162.

In order to form the separation distance d4, a sealing member 150" according to an exemplary embodiment may be provided. To form a large distance d4 between the transparent member 140 and the board 161 for accommodating the connector 166, the height of the sealing member 150" in the third direction (Z direction) of FIG. 25 is greater than that of the sealing member 150 of FIG. 16.

In addition, the sealing member 150" according to an exemplary embodiment may be formed to have different heights based on the coupling groove for fastening the transparent member 140.

For example, as illustrated in FIG. 30, the height d4 of the sealing member 150" in the third direction corresponding to the transparent member 140 and the board 161 may be formed relatively large in order to form a separation distance to accommodate the connector 166. In contrast, the height d7 in the third direction of the sealing member 150" for providing the waterproof of the seating part 134 and transparent member 140 is formed to be less than the height d4 in the third direction.

In some exemplary embodiments, the connector 166 may be mounted on the bottom surface of the board 161. In this case, the cross-section of the light source unit 162 is similar to that of FIG. 16, except that the connector 166 is mounted on the bottom surface of the board 161, and thus, repeated descriptions thereof will be omitted.

Figure 31:
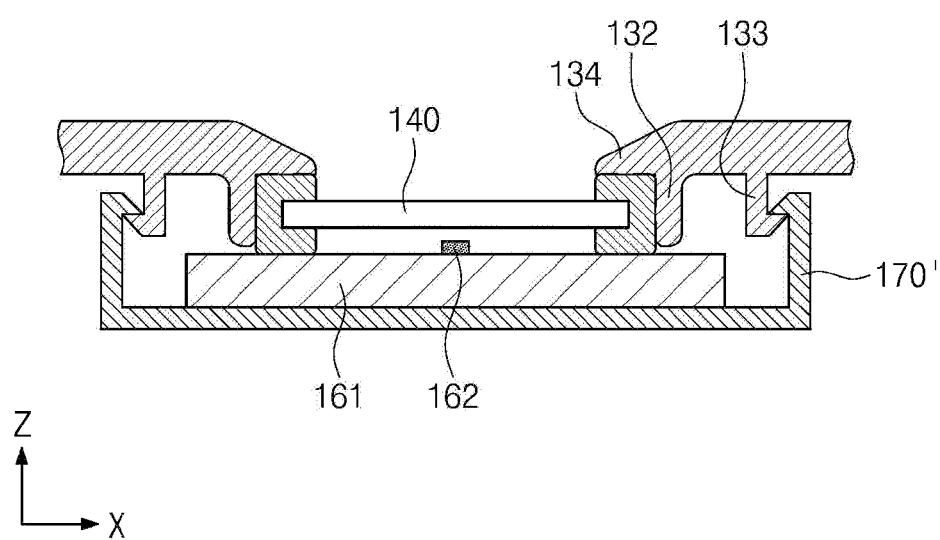
FIG. 31 is a perspective view of a sterilization module according to an exemplary embodiment.

FIG. 31 is a perspective view illustrating a sterilization module 100''' according to an exemplary embodiment. The sterilization module 100''' of FIG. 31 is similar to the sterilization module 100 described in FIGS. 1 to 19. Accordingly, the same or similar elements will be denoted using the same or similar reference numerals, and repeated descriptions thereof will be omitted.

Referring to FIG. 31, the sterilization module 100''' according to an exemplary embodiment may include a main body coupling part 133 and a fastening member 170' that fix the board 161 to the main body 110 by a hook coupling method.

While the sterilization module 100 shown in FIGS. 1 and 5 fixes the board 161 to the main body 110 by a screw coupling method, the sterilization module 100''' of FIG. 31 is connected to the hook coupling method by fixing the board 161 to the main body 110.

As such, a hook-shaped main body coupling portion 133 protruding toward the inside of the main body 110 is formed on the lower surface of the upper body 130. In addition, the fastening member 170' has a hook shape, in which both ends protrude toward the inside of the main body 110. When the board 161 is coupled to the main body 110, the main body coupling portion 133 and the fastening member 170' are hooked to each other so that the board 161 may be firmly fixed to the main body 110.

The sterilization module according to exemplary embodiments may facilitate miniaturization, and the sterilization efficiency may also be increased.

The sterilization module according to exemplary embodiments has a structure capable of preventing leakage, thereby preventing the sterilization module from failing due to water penetrating the inside of the sterilization module.

In addition, according to exemplary embodiments, electrical defects in the device may be prevented from occurring due to water penetrating along the sterilization module into the device, in which the sterilization module is installed.

Moreover, according to exemplary embodiments, because the size of the sterilization module may be minimized, the sterilization module may be applied over a wide range of fields, and the water leakage to the sterilization module installation part may be prevented.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A sterilization module comprising:
a main body including an ultraviolet outlet;
a transparent member disposed on the ultraviolet outlet and configured to transmit ultraviolet light;
a light source unit configured to irradiate ultraviolet light toward the transparent member; and
a sealing member,
wherein the light source unit includes:
a circuit board; and
a light emitting diode chip mounted on the circuit board, and including:
an epitaxial substrate;
a conductive semiconductor layer formed on the epitaxial substrate; and
an electrode,
wherein the conductive semiconductor layer of the light emitting diode chip is electrically connected to the circuit board directly by the electrode,
wherein ultraviolet light is configured to be irradiated toward the transparent member by passing through the epitaxial substrate,
wherein the sealing member forms a space, in which the light emitting diode chip is disposed, the sealing member being disposed between the transparent member and the circuit board, and
wherein a distance between the transparent member and the circuit board spaced apart from each other by the sealing member is greater than a height of the light emitting diode chip.

2. The sterilization module of claim 1, wherein
the electrode is electrically connected to the circuit board, and is
bonded to the circuit board a bonding material.

3. The sterilization module of claim 2, wherein the bonding material includes a conductive material of at least one of silver (Ag), tin (Sn), or copper (Cu).

4. The sterilization module of claim 1, wherein the sealing member has a shape in which a top surface and a bottom surface are opened, and
wherein the sealing member includes a coupling groove disposed in an interior thereof to which the transparent member is to be inserted.

5. The sterilization module of claim 4, wherein the sealing member includes a protrusion protruding from at least one of a top surface, a bottom surface, and a side surface of the sealing member.

6. The sterilization module of claim 1, wherein the main body includes:
an upper body in which the ultraviolet outlet is formed; and
a lower body positioned under the upper body and providing a space in which the light source unit is to be installed,
wherein a top surface of the sealing member is in close contact with a bottom surface of the upper body, and
wherein the upper body includes a seating part formed along a circumference of the ultraviolet outlet.

7. The sterilization module of claim 6, wherein the upper body has a bottom surface including a guide extending in a first direction and is in close contact with a side surface of the sealing member, and
wherein a length of the sealing member in the first direction is greater than a length of the guide in the first direction.

8. The sterilization module of claim 7, wherein the bottom surface of the upper body includes a main body coupling part extending in the first direction to fix the circuit board to the upper body and
wherein a length of the main body coupling part in the first direction is equal to a length of the sealing member in the first direction.

9. The sterilization module of claim 8, further comprising:
a fastening member penetrating the circuit board and coupled to the main body coupling part,
wherein, when the fastening member is coupled to the main body coupling part, the fastening member is configured to pressurize the circuit board, the circuit board is configured to pressurize the sealing member, and the sealing member is configured to be elastically reduced by the pressure between the seating part and the circuit board.

10. The sterilization module of claim 9, wherein the fastening member is a screw, and
wherein a screw groove is formed on an inner wall of the main body coupling part.

11. The sterilization module of claim 9, wherein the fastening member includes a hook to be coupled to the main body coupling part.

12. The sterilization module of claim 9, wherein the circuit board includes:
a light source module coupling part through which the fastening member penetrates; and
a connecting passage for drawing a wire to supply power to the light source unit from an outside.

13. The sterilization module of claim 12, further comprising:
a plurality of support members in close contact with a bottom surface of the upper body and a side surface of the lower body,
wherein at least one of the plurality of support members is exposed to an outside through the connecting passage,
wherein the main body coupling part for fixing the circuit board to the upper body is formed on a bottom surface of the upper body, and
wherein at least a part of a side surface of the guide is in contact with the main body coupling part.

14. The sterilization module of claim 1, wherein the main body includes:
an upper body in which the ultraviolet outlet is formed; and
a lower body positioned under the upper body and providing a space in which the light source unit is installed,
wherein the sealing member includes:
a first sealing member interposed between the upper body and the transparent member; and
a second sealing member interposed between the transparent member and the circuit board and different from the first sealing member.

15. The sterilization module of claim 1, further comprising:
- a connector mounted on the circuit board and electrically connected to the light source unit,
- wherein a distance between the transparent member and the circuit board spaced apart from each other by the sealing member is greater than a height of the connector.

16. A sterilization module comprising:
- a main body including a through pipe having a first shape cross-section;
- a light source unit provided in the through pipe of the main body and having a second shape different from the first shape;
- a transparent member provided in an optical path of light emitted from the light source unit and sealing one side of the through pipe;
- a waterproof resin filled inside the main body and sealing the other end of the through pipe; and
- a sealing member provided inside the main body and sealing a gap between the through pipe and the light source unit,
- wherein the light source unit includes:
  - a board having a first surface and a second surface; and
  - a light emitting diode disposed on the first surface of the board and configured to emit light,
- wherein the waterproof resin is provided on the second surface of the board, and
- wherein the board has the second shape.

17. The sterilization module of claim 16, wherein the waterproof resin and the transparent member are spaced apart from each other with the board interposed therebetween.

18. The sterilization module of claim 16, further comprising:
- an outer holder coupled to the main body,
- wherein the outer holder includes an outer holder coupling part configured to be coupled to an outer wall of a reservoir, and
- wherein a size of a cross-section of the outer holder coupling part is less than a size of a cross-section of the through pipe.

19. A sterilization module comprising:
- a main body including a through pipe;
- a light source unit provided inside the through pipe of the main body;
- a transparent member provided in an optical path of light emitted from the light source unit and sealing one side of the through pipe; and
- a waterproof resin filled inside the main body and sealing the other end of the through pipe,
- wherein the light source unit includes:
  - a board having a first surface and a second surface; and
  - a light emitting diode disposed on the first surface of the board and configured to emit light,
- wherein the board includes a wiring part,
- wherein the light emitting diode is electrically connected to the wiring part of the board directly,
- wherein the light emitting diode is provided in a form a chip to emit light toward the transparent member directly without a lens and a case, and
- wherein the waterproof resin is disposed on the second surface of the board.

20. The sterilization module of claim 19, wherein the waterproof resin is in contact with the second surface of the board.

21. The sterilization module of claim 19, further comprising:
- an outer holder coupled to the main body,
- wherein the outer holder includes an outer holder coupling part configured to be coupled to an outer wall of a reservoir, and
- wherein a size of a cross-section of the outer holder coupling part is less than a size of a cross-section of the through pipe.

* * * * *